United States Patent
Jaeschke et al.

(10) Patent No.: US 7,511,055 B2
(45) Date of Patent: Mar. 31, 2009

(54) NAPHTHYRIDIN DERIVATIVES

(75) Inventors: Georg Jaeschke, Basel (CH); Sabine Kolczewski, Rheinfelden (DE); Richard Hugh Philip Porter, Reinach (CH); Patrick Schnider, Bottmingen (CH); Eric Vieira, Frenkendorf (CH)

(73) Assignee: Hoffmann-La Roche Inc., Nutley, NJ (US)

( * ) Notice: Subject to any disclaimer, the term of this patent is extended or adjusted under 35 U.S.C. 154(b) by 224 days.

(21) Appl. No.: 11/529,992

(22) Filed: Sep. 28, 2006

(65) Prior Publication Data

US 2007/0078155 A1 Apr. 5, 2007

(30) Foreign Application Priority Data

Oct. 5, 2005 (EP) .................. 05109241

(51) Int. Cl.
*C07D 471/02* (2006.01)
*A01N 43/42* (2006.01)
*A61K 31/44* (2006.01)

(52) U.S. Cl. ...................... 514/300; 546/122
(58) Field of Classification Search .............. 546/122; 514/300
See application file for complete search history.

(56) References Cited

U.S. PATENT DOCUMENTS

| 4,659,710 A | 4/1987 | Sato et al. |
| 4,690,924 A | 9/1987 | Sato et al. |

FOREIGN PATENT DOCUMENTS

| WO | WO 02/28837 A1 | 4/2002 |
| WO | WO 02/44189 | 6/2002 |
| WO | 2004/058729 | * 7/2004 |
| WO | WO 2004/058729 A1 | 7/2004 |
| WO | WO 2004/076420 | 9/2004 |
| WO | WO 2004/081001 | 9/2004 |
| WO | WO 2005/079802 | 9/2005 |

OTHER PUBLICATIONS

Filipski, et al., *A versatile copper-catalyzed coupling reaction of pyridine-2(1H)-ones with aryl halides*, Tetrahedron Letters, vol. 47, No. 44, pp. 7677-7680 (2006), XP005669960.
P. Molina, et al., *Iminophosphorane-mediated annelation of a pyridine ring into a preformed pyridine one: Synthesis of naphthyridine, pyridol[1,2-c] pyrimidine and pyrido [1,2-c] quinazoline derivatives*, Tetrahedron, vol. 48, No. 22, pp. 4601-4616 (1992), XP002415037.
Bonnefous et al., Bioorganic & Medicinal Chemistry Letters, vol. 15, pp. 1197-1200 (2005).
Mutel, V., Expert Opin, Ther. Patents, vol. 12(12) pp. 1845-1852 (2002).
Epsztajn, et al., Synthetic Communications, vol. 27(6), pp. 1075-1086 (1997).
Schlaeger, et al., Cytotechnology, vol. 30, pp. 71-83 (1999).
Porter, et al., British Journal of Pharmacology, vol. 128, pp. 13-20 (1999).
Sanchez, et al., J. Heterocycl. Chem. vol. 24, pp. 215-217 (1987).
Jinaraj, et al., Indian J. Chem., vol. 22B, pp. 841-845 (1983).
Smith, et al., J. Org. Chem. vol. 20, pp. 829-838 (1955).
Iwasaki, et al., J. Med. Chem. vol. 38, pp. 496-507 (1995).
Abstract corresponding to WO 04/081001 (B1) (2004).
Abstract corresponding to WO 04/076420 (B2) (2004).
Woźniak et al., Journal of Heterocyclic Chemistry (1978), vol. 15(5) pp. 731-736.
Storto et al., European Journal of Pharmacology (2004) vol. 497(1), pp. 25-27.
Storto, et al., Journal of Hepatology (2003) vol. 38(2), pp. 179-187.
Storto et al., Hepatology (Philadelphia) (2000) vol. 31(3) pp. 649-655.
Sakamoto, et al., Chem. Pharm. Bull. (1985) vol. 33(2), pp. 626-633.

* cited by examiner

*Primary Examiner*—D. Margaret Seaman
*Assistant Examiner*—Niloofar Rahmani
(74) *Attorney, Agent, or Firm*—George W. Johnston; Patricia S. Rocha-Tramaloni; Kimberly J. Prior

(57) ABSTRACT

The present invention relates to heterocyclic derivatives of formula I

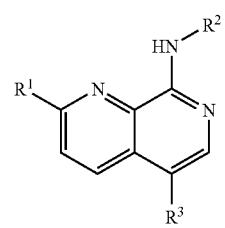

wherein $R^1$, $R^2$ and $R^3$ are as defined in the description and claims, which compounds are metabotropic glutamate receptor 5 antagonists.

20 Claims, No Drawings

NAPHTHYRIDIN DERIVATIVES

PRIORITY TO RELATED APPLICATIONS

This application claims the benefit of European Application No. 05109241.9, filed Oct. 5, 2005, which is hereby incorporated by reference in its entirety.

BACKGROUND OF THE INVENTION

In the central nervous system (CNS) the transmission of stimuli takes place by the interaction of a neurotransmitter, which is sent out by a neuron, with a neuroreceptor.

Glutamate is the major excitatory neurotransmitter in the brain and plays a unique role in a variety of central nervous system (CNS) functions. The glutamate-dependent stimulus receptors are divided into two main groups. The first main group, namely the ionotropic receptors, forms ligand-controlled ion channels. The metabotropic glutamate receptors (mGluR) belong to the second main group and, furthermore, belong to the family of G-protein coupled receptors.

At present, eight different members of these mGluR are known and of these some even have sub-types. According to their sequence homology, signal transduction mechanisms and agonist selectivity, these eight receptors can be sub-divided into three sub-groups:

mGluR1 and mGluR5 belong to group I, mGluR2 and mGluR3 belong to group II and mGluR4, mGluR6, mGluR7 and mGluR8 belong to group III.

Ligands of metabotropic glutamate receptors belonging to the first group can be used for the treatment or prevention of acute and/or chronic neurological disorders such as psychosis, epilepsy, schizophrenia, Alzheimer's disease, cognitive disorders and memory deficits, as well as chronic and acute pain.

Other treatable indications in this connection are restricted brain function caused by bypass operations or transplants, poor blood supply to the brain, spinal cord injuries, head injuries, hypoxia caused by pregnancy, cardiac arrest and hypoglycaemia. Further treatable indications are ischemia, Huntington's chorea, amyotrophic lateral sclerosis (ALS), dementia caused by AIDS, eye injuries, retinopathy, idiopathic parkinsonism or parkinsonism caused by medicaments as well as conditions which lead to glutamate-deficiency functions, such as e.g. muscle spasms, convulsions, migraine, urinary incontinence, nicotine addiction, opiate addiction, anxiety, vomiting, dyskinesia, gastrointestinal reflux disorder and depressions.

Disorders mediated full or in part by mGluR5 are for example acute, traumatic and chronic degenerative processes of the nervous system, such as Alzheimer's disease, senile dementia, Parkinson's disease, Huntington's chorea, amyotrophic lateral sclerosis and multiple sclerosis, psychiatric diseases such as schizophrenia and anxiety, depression, pain and drug dependency (*Expert Opin. Ther. Patents* (2002), 12, (12)).

SUMMARY OF THE INVENTION

The present invention provides heterocyclic derivatives of formula I

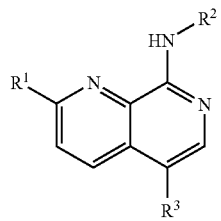

wherein
$R^1$ is hydrogen, halogen, cyano, lower alkoxy, lower alkyl, lower alkyl substituted by halogen, cycloalkyl, —$(CH_2)_n$—O-lower alkyl, or —C(O)R' wherein R' is lower alkyl, lower alkoxy or $NR_2$;
R is hydrogen or lower alkyl;
$R^2$ is aryl or 5- or 6-membered heteroaryl;
$R^3$ is hydrogen, OR, $NR_2$, lower alkyl, cycloalkyl, aryl, heterocycloalkyl, 5- or 6-membered heteroaryl, C(O)$NR_2$, lower alkyl substituted by halogen, or —C(O)R' wherein R' is lower alkyl, lower alkoxy or $NR_2$;
    wherein the aryl, cycloalkyl, heterocycloalkyl or 5- or 6-membered heteroaryl groups for $R^2$ and $R^3$ are unsubstituted or substituted by:
    halogen,
    cyano,
    lower alkyl optionally substituted by one or more halogen atoms,
    lower alkoxy,
    $S(O)_2$-alkyl,
    $S(O)$-alkyl, or
    —C(O)R' wherein R' is lower alkyl, lower alkoxy or $NR_2$; and
n is 0, 1 or 2;

and to pharmaceutically acceptable salts thereof.

The present invention also provides pharmaceutical compositions containing compounds of the invention and methods for the manufacture of such compounds and compositions.

Compounds of formula I are metabotropic glutamate receptor antagonists. Compounds of formula I are distinguished by having valuable therapeutic properties. They can be used in the treatment or prevention of mGluR5 receptor mediated disorders.

Such disorders are acute and/or chronic neurological disorders, in particular acute or chronic pain, urinary incontinence, gastrointestinal reflux disorder, liver damage or failure whether drug or disease induced, obesity or Fragile-X or autism, acute, traumatic and chronic degenerative processes of the nervous system, such as Alzheimer's disease, senile dementia, Parkinson's disease, Huntington's chorea, amyotrophic lateral sclerosis and multiple sclerosis, psychiatric diseases such as schizophrenia and anxiety, depression and drug dependency.

DETAILED DESCRIPTION OF THE INVENTION

The following definitions of general terms used in the present description apply irrespective of whether the terms in question appear alone or in combination. It must be noted that, as used in the specification and the appended claims, the singular forms "a", "an," and "the" include plural forms unless the context clearly dictates otherwise.

The term "lower alkyl" used in the present description denotes straight-chain or branched saturated hydrocarbon residues with 1 to 6 carbon atoms, preferably with 1 to 4 carbon atoms, such as methyl, ethyl, n-propyl, i-propyl, n-butyl, t-butyl and the like.

The term "lower alkoxy" denotes a lower alkyl residue in the sense of the foregoing definition bound via an oxygen atom. Examples of "lower alkoxy" residues include methoxy, ethoxy, isopropoxy and the like.

The term "halogen" denotes fluorine, chlorine, bromine and iodine.

The term "lower alkyl substituted by halogen" denotes a lower alkyl group as defined above which is substituted by one or more halogen atoms. Examples of such groups include, but are not limited to, methyl, ethyl, propyl, isopropyl, isobutyl, sec-butyl, tert-butyl, pentyl or n-hexyl substituted by one or more Cl, F, Br or I atom(s) as well as those groups specifically illustrated by the examples herein below. Preferred groups are difluoro- or trifluoro-methyl or ethyl.

"Aryl" represents an aromatic carbocyclic group consisting of one individual ring, or one or more fused rings in which at least one ring is aromatic in nature. Preferred aryl group is phenyl.

The term "5- or 6-membered heteroaryl" refers to an aromatic ring containing five or six ring atoms, respectively, wherein one or more of the ring atoms is a heteroatom(s) selected from nitrogen, oxygen and sulphur, with the other ring members being carbon atoms. Preferred are those heteroaryl groups containing a nitrogen atom. Examples of such heteroaryl groups are imidazolyl, isoxazolyl, pyrazinyl, pyrazolyl, pyridazinyl, pyridinyl, pyrimidinyl, thiadiazolyl or thiazolyl.

The term "heterocycloalkyl" refers to a saturated non aromatic ring containing one or more heteroatom selected from nitrogen, oxygen and sulphur, with the rest of the ring members being carbon atoms. Preferred are those heterocycloalkyl groups selected from nitrogen. Examples of such groups are morpholinyl, tetrahydropyranyl, thiomorpholinyl, piperazinyl, pyrrolidinyl or piperidyl.

The term "cycloalkyl" denotes a saturated carbocyclic group, containing 3-12 carbon atoms, preferably 3-6 carbon atoms.

"Pharmaceutically acceptable," such as pharmaceutically acceptable carrier, excipient, etc., means pharmacologically acceptable and substantially non-toxic to the subject to which the particular compound is administered.

The term "pharmaceutically acceptable salt" refers to any salt derived from an inorganic or organic acid or base. Such salts include: acid addition salts formed with inorganic acids such as hydrochloric acid, hydrobromic acid, sulfuric acid, nitric acid, phosphoric acid; or formed with organic acids such as acetic acid, benzenesulfonic acid, benzoic, camphorsulfonic acid, citric acid, ethanesulfonic acid, fumaric acid, glucoheptonic acid, gluconic acid, glutamic acid, glycolic acid, hydroxynaphtoic acid, 2-hydroxyethanesulfonic acid, lactic acid, maleic acid, malic acid, malonic acid, mandelic acid, methanesulfonic acid, muconic acid, 2-naphthalenesulfonic acid, propionic acid, salicylic acid, succinic acid, tartaric acid, p-toluenesulfonic acid or trimethylacetic acid.

"Therapeutically effective amount" means an amount that is effective to prevent, alleviate or ameliorate symptoms of disease or prolong the survival of the subject being treated.

The present invention provides heterocyclic derivatives of formula I

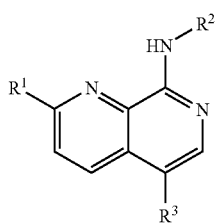

wherein
$R^1$ is hydrogen, halogen, cyano, lower alkoxy, lower alkyl, lower alkyl substituted by halogen, cycloalkyl, —$(CH_2)_n$—O-lower alkyl, —C(O)R' wherein R' is lower alkyl, lower alkoxy or $NR_2$;
R is hydrogen or lower alkyl;
$R^2$ is aryl or 5- or 6-membered heteroaryl;
$R^3$ is hydrogen, OR, $NR_2$, lower alkyl, cycloalkyl, aryl, heterocycloalkyl, 5- or 6-membered heteroaryl, $C(O)NR_2$, lower alkyl substituted by halogen, or —C(O)R' wherein R' is lower alkyl, lower alkoxy or $NR_2$;
wherein the aryl, cycloalkyl, heterocycloalkyl or 5- or 6-membered heteroaryl groups for $R^2$ and $R^3$ are unsubstituted or substituted by:
  halogen,
  cyano,
  lower alkyl optionally substituted by one or more halogen atoms,
  lower alkoxy,
  $S(O)_2$-alkyl,
  S(O)-alkyl, or
  —C(O)R' wherein R' is lower alkyl, lower alkoxy or $NR_2$;
n is 0, 1 or 2;

and to pharmaceutically acceptable salts thereof.

Preferred compounds of formula I are compounds wherein

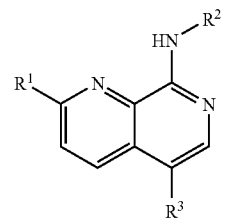

wherein
$R^1$ is hydrogen or lower alkyl;
$R^2$ is aryl or 5- or 6-membered heteroaryl;
$R^3$ is hydrogen, aryl or 5- or 6-membered heteroaryl;

wherein the aryl or 5- or 6-membered heteroaryl groups for $R^2$ and $R^3$ are unsubstituted or substituted by:
  halogen,
  lower alkyl optionally substituted by one or more halogen atoms,
  lower alkoxy,
  —C(O)O-lower alkyl or
  cyano.

Other preferred compounds of formula I are those, in which $R^3$ is hydrogen, for example, those compounds wherein $R^3$ is hydrogen and $R^2$ is 5- or 6-membered substituted heteroaryl, for example the following compounds:
(6-methyl-pyridin-2-yl)-[1,7]naphthyridin-8-yl-amine,
(4-methyl-thiazol-2-yl)-[1,7]naphthyridin-8-yl-amine,
(2-Methyl-[1,7]naphthyridin-8-yl)-(4-methyl-thiazol-2-yl)-amine,
(5-Chloro-pyridin-2-yl)-(2-methyl-[1,7]naphthyridin-8-yl)-amine,
(5-Fluoro-pyridin-2-yl)-(2-methyl-[1,7]naphthyridin-8-yl)-amine,
(2-Chloro-pyridin-4-yl)-(2-methyl-[1,7]naphthyridin-8-yl)-amine,
(2-Methyl-[1,7]naphthyridin-8-yl)-(1-methyl-1H-pyrazol-3-yl)-amine,
(2-Methyl-[1,7]naphthyridin-8-yl)-(2-methyl-thiazol-4-yl)-amine,
(2-Chloro-[1,7]naphthyridin-8-yl)-(4-methyl-thiazol-2-yl)-amine,
(2-Chloro-[1,7]naphthyridin-8-yl)-(2-methyl-thiazol-4-yl)-amine,
(2-Methoxy-[1,7]naphthyridin-8-yl)-(4-methyl-thiazol-2-yl)-amine, and
(2-Ethyl-[1,7]naphthyridin-8-yl)-(4-methyl-thiazol-2-yl)-amine.

Further preferred are compounds, wherein R³ is hydrogen and R² is substituted aryl, for example the following compounds:
(3-chloro-phenyl)-[1,7]naphthyridin-8-yl-amine, and
(3-Chloro-phenyl)-(2-methyl-[1,7]naphthyridin-8-yl)-amine.

Still further preferred compounds of formula I are further those, wherein R³ is a 5- or 6-membered optionally substituted heteroaryl. Among these compounds, preferred compounds are those wherein R³ and R² are both 5- or 6-membered optionally substituted heteroaryl, for example the following compounds:
(6-methyl-pyridin-2-yl)-(5-pyridin-3-yl-[1,7]naphthyridin-8-yl)-amine,
(2-chloro-pyridin-4-yl)-(5-pyridin-3-yl-[1,7]naphthyridin-8-yl)-amine,
(5-methyl-pyridin-2-yl)-(5-pyridin-3-yl-[1,7]naphthyridin-8-yl)-amine,
(5-fluoro-pyridin-2-yl)-(5-pyridin-3-yl-[1,7]naphthyridin-8-yl)-amine,
(2-chloro-pyridin-4-yl)-[5-(6-methoxy-pyridin-3-yl)-[1,7]naphthyridin-8-yl]-amine,
(2-chloro-pyridin-4-yl)-[5-(5-fluoro-pyridin-3-yl)-[1,7]naphthyridin-8-yl]-amine,
(5-fluoro-pyridin-2-yl)-[5-(5-fluoro-pyridin-3-yl)-[1,7]naphthyridin-8-yl]-amine,
(5-fluoro-pyridin-2-yl)-[5-(5-methoxy-pyridin-3-yl)-[1,7]naphthyridin-8-yl]-amine,
(2-chloro-pyridin-4-yl)-(5-pyrimidin-5-yl-[1,7]naphthyridin-8-yl)-amine,
(5-fluoro-pyridin-2-yl)-(5-pyrimidin-5-yl-[1,7]naphthyridin-8-yl)-amine,
(4-Methyl-thiazol-2-yl)-(5-pyrimidin-5-yl-[1,7]naphthyridin-8-yl)-amine,
(4-Methyl-thiazol-2-yl)-(5-pyridin-3-yl-[1,7]naphthyridin-8-yl)-amine,
(1-Methyl-1H-pyrazol-3-yl)-(5-pyridin-3-yl-[1,7]naphthyridin-8-yl)-amine,
(2-Methyl-thiazol-4-yl)-(5-pyridin-3-yl-[1,7]naphthyridin-8-yl)-amine,
(2-Methyl-thiazol-4-yl)-(5-pyrimidin-5-yl-[1,7]naphthyridin-8-yl)-amine,
(2-Methyl-5-pyridin-3-yl-[1,7]naphthyridin-8-yl)-(4-methyl-thiazol-2-yl)-amine,
(5-Fluoro-pyridin-2-yl)-(2-methyl-5-pyridin-3-yl-[1,7]naphthyridin-8-yl)-amine,
(2-Methyl-5-pyridin-3-yl-[1,7]naphthyridin-8-yl)-(2-methyl-thiazol-4-yl)-amine,
(2-Chloro-pyridin-4-yl)-(2-methyl-5-pyridin-3-yl-[1,7]naphthyridin-8-yl)-amine,
(2-Methyl-5-pyrimidin-5-yl-[1,7]naphthyridin-8-yl)-(2-methyl-thiazol-4-yl)-amine,
[5-(6-Chloro-pyridin-3-yl)-2-methyl-[1,7]naphthyridin-8-yl]-(2-methyl-thiazol-4-yl)-amine,
[5-(6-Chloro-pyridin-3-yl)-2-methyl-[1,7]naphthyridin-8-yl]-(4-methyl-thiazol-2-yl)-amine,
[5-(3,5-Dimethyl-isoxazol-4-yl)-2-methyl-[1,7]naphthyridin-8-yl]-(4-methyl-thiazol-2-yl)-amine,
[5-(2,5-Dimethyl-2H-pyrazol-3-yl)-2-methyl-[1,7]naphthyridin-8-yl]-(4-methyl-thiazol-2-yl)-amine,
5-[2-Methyl-8-(4-methyl-thiazol-2-ylamino)-[1,7]naphthyridin-5-yl]-pyridine-2-carbonitrile,
(2-Methyl-5-pyrimidin-5-yl-[1,7]naphthyridin-8-yl)-(4-methyl-thiazol-2-yl)-amine,
(2-Methyl-5-pyridin-4-yl-[1,7]naphthyridin-8-yl)-(4-methyl-thiazol-2-yl)-amine,
[2-Methyl-5-(4-methyl-pyridin-3-yl)-[1,7]naphthyridin-8-yl]-(4-methyl-thiazol-2-yl)-amine,
[5-(6-Fluoro-pyridin-3-yl)-2-methyl-[1,7]naphthyridin-8-yl]-(4-methyl-thiazol-2-yl)-amine,
[5-(6-Methoxy-pyridin-3-yl)-2-methyl-[1,7]naphthyridin-8-yl]-(4-methyl-thiazol-2-yl)-amine,
[5-(5-Methoxy-pyridin-3-yl)-2-methyl-[1,7]naphthyridin-8-yl]-(4-methyl-thiazol-2-yl)-amine,
[2-Methyl-5-(3-methyl-pyridin-2-yl)-[1,7]naphthyridin-8-yl]-(4-methyl-thiazol-2-yl)-amine,
(2-Methyl-5-pyrimidin-5-yl-[1,7]naphthyridin-8-yl)-(4-trifluoromethyl-thiazol-2-yl)-amine,
(4-Chloro-thiazol-2-yl)-(2-methyl-5-pyrimidin-5-yl-[1,7]naphthyridin-8-yl)-amine,
[5-(5-Fluoro-pyridin-3-yl)-2-methyl-[1,7]naphthyridin-8-yl]-(4-methyl-thiazol-2-yl)-amine,
[2-Methyl-5-(6-methyl-pyridin-3-yl)-[1,7]naphthyridin-8-yl]-(4-methyl-thiazol-2-yl)-amine,
(2-Methyl-pyrimidin-4-yl)-(2-methyl-5-pyrimidin-5-yl-[1,7]naphthyridin-8-yl)-amine,
(2-Chloro-pyridin-4-yl)-(2-methyl-5-pyrimidin-5-yl-[1,7]naphthyridin-8-yl)-amine,
[5-(2,5-Dimethyl-2H-pyrazol-3-yl)-2-methyl-[1,7]naphthyridin-8-yl]-(2-methyl-thiazol-4-yl)-amine,
(2-Methyl-5-pyrimidin-2-yl-[1,7]naphthyridin-8-yl)-(2-methyl-thiazol-4-yl)-amine,
[2-Methyl-5-(2-methyl-pyridin-3-yl)-[1,7]naphthyridin-8-yl]-(2-methyl-thiazol-4-yl)-amine,
(1-Methyl-1H-pyrazol-3-yl)-(2-methyl-5-pyrimidin-5-yl-[1,7]naphthyridin-8-yl)-amine,
[5-(5-Fluoro-pyridin-3-yl)-2-methyl-[1,7]naphthyridin-8-yl]-(1-methyl-1H-pyrazol-3-yl)-amine,
[2-Methyl-5-(6-methyl-pyridin-2-yl)-[1,7]naphthyridin-8-yl]-(2-methyl-thiazol-4-yl)-amine,
(4-Methyl-thiazol-2-yl)-(2-methyl-5-thiazol-2-yl-[1,7]naphthyridin-8-yl)-amine,
[2-Methyl-5-(3-methyl-3H-imidazol-4-yl)-[1,7]naphthyridin-8-yl]-(4-methyl-thiazol-2-yl)-amine,
[2-Methyl-5-(3-methyl-3H-imidazol-4-yl)-[1,7]naphthyridin-8-yl]-(2-methyl-thiazol-4-yl)-amine,
[2-Methyl-5-(3-methyl-[1,2,4]thiadiazol-5-yl)-[1,7]naphthyridin-8-yl]-(2-methyl-thiazol-4-yl)-amine,
[2-Methyl-5-(2-methyl-pyrimidin-5-yl)-[1,7]naphthyridin-8-yl]-(2-methyl-thiazol-4-yl)-amine,
(2-Methyl-5-pyrazin-2-yl-[1,7]naphthyridin-8-yl)-(2-methyl-thiazol-4-yl)-amine,
[5-(5-Fluoro-pyridin-3-yl)-2-methyl-[1,7]naphthyridin-8-yl]-(2-methyl-thiazol-4-yl)-amine,
(2-Methyl-5-pyridin-3-yl-[1,7]naphthyridin-8-yl)-(4-trifluoromethyl-thiazol-2-yl)-amine,
(4-Difluoromethyl-thiazol-2-yl)-(2-methyl-5-pyridin-3-yl-[1,7]naphthyridin-8-yl)-amine,
(4-Methyl-thiazol-2-yl)-[2-methyl-5-(5-trifluoromethyl-pyridin-3-yl)-[1,7]naphthyridin-8-yl]-amine, and
(4-Methyl-thiazol-2-yl)-[2-methyl-5-(6-trifluoromethyl-pyrazin-2-yl)-[1,7]naphthyridin-8-yl]-amine.

Further preferred compounds of formula I are further those, wherein R³ is 5- or 6-membered substituted heteroaryl and R² is substituted aryl, for example the following compounds:
(3-chloro-phenyl)-(5-pyridin-3-yl-[1,7]naphthyridin-8-yl)-amine, and
(3-chloro-phenyl)-[5-(6-chloro-pyridin-3-yl)-[1,7]naphthyridin-8-yl]-amine.

Other preferred compounds of formula I are those, wherein R³ is optionally substituted aryl, for example, compounds in which R³ is substituted aryl and R² is 5- or 6-membered-substituted heteroaryl, for example the following compounds:
[5-(3-Methoxy-phenyl)-2-methyl-[1,7]naphthyridin-8-yl]-(4-methyl-thiazol-2-yl)-amine,
(4-Methyl-thiazol-2-yl)-[2-methyl-5-(3-trifluoromethyl-phenyl)-[1,7]naphthyridin-8-yl]-amine,

[5-(3-Methanesulfonyl-phenyl)-2-methyl-[1,7]naphthyridin-8-yl]-(4-methyl-thiazol-2-yl)-amine, and
[5-(3-Fluoro-phenyl)-2-methyl-[1,7]naphthyridin-8-yl]-(1-methyl-1H-pyrazol-3-yl)-amine.

The compounds of formula I of the invention can be prepared according to various processes.

In an embodiment, the process of the invention comprises the following variants a) reacting a compound of formula

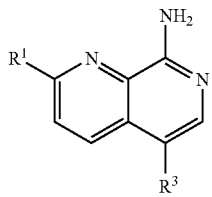

II with a compound of formula $R^2Br$ to obtain a compound of formula

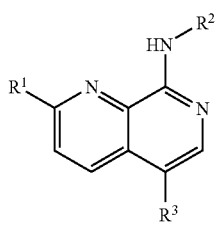

I wherein $R^1$, $R^2$ and $R^3$ are as defined above, and if desired, converting the compounds obtained into pharmaceutically acceptable acid addition salts, or b) reacting a compound of formula

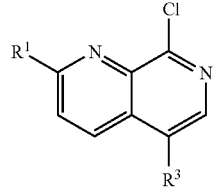

III with a compound of formula $NH_2R^2$ to obtain a compound of formula

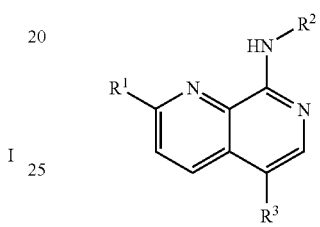

I wherein $R^1$, $R^2$ and $R^3$ are as defined above, and if desired, converting the compounds obtained into pharmaceutically acceptable acid addition salts.

The various processes of the invention are described in more detail in the following schemes 1-3 and in examples 1-81.

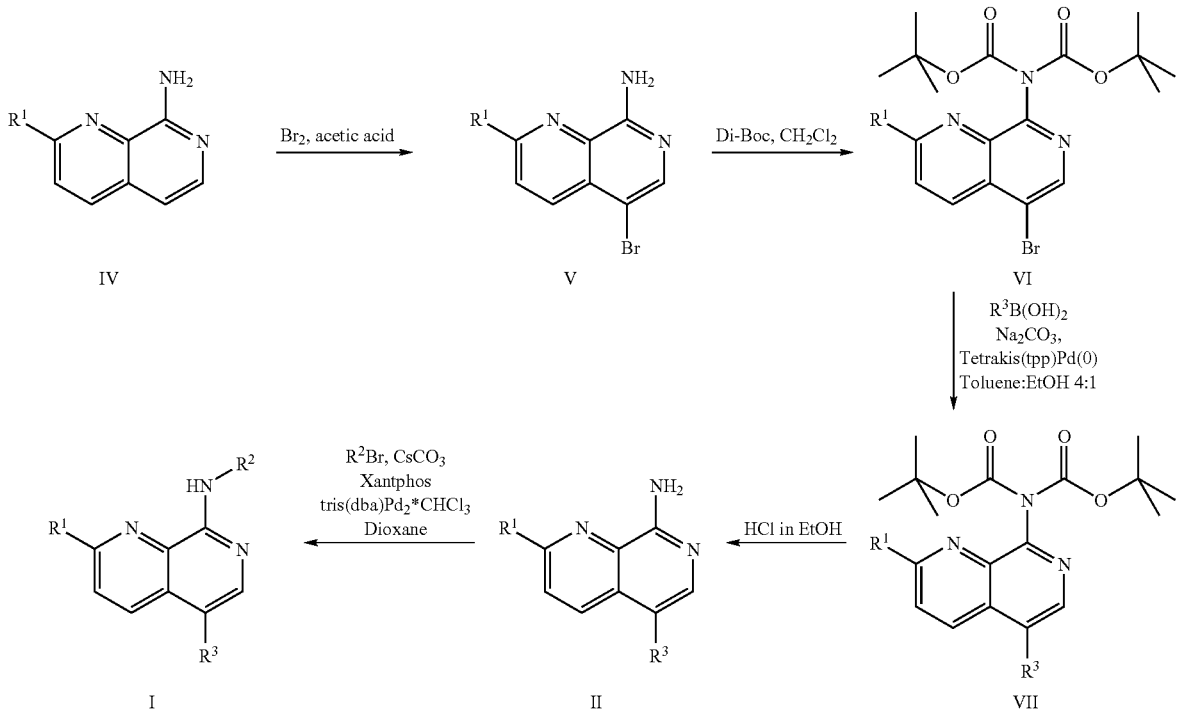

Scheme 1 wherein the substituents $R^1$, $R^2$ and $R^3$ are as described above.

In more detail, the compounds of formula I can be prepared as follows:

In accordance with Scheme 1, the compounds of formula V can be prepared in accordance with methods known in the art and commercially available starting products, for example as described in Journal of Heterocyclic Chemistry, 1978, 15(5), 731-6.

Furthermore, compounds of formula V, for example 5-bromo-[1,7]naphthyridin-8-ylamine, di-tert.-butyldicarbonate and 4-(N,N-dimethylamino)pyridine are N-protected, e.g. with a di-Boc group e.g. by dissolving in dichloromethane and refluxing for about 2 hrs to obtain a compound of formula VI. Then Tetrakis(triphenylphosphine)palladium (0) is dissolved in toluene. A compound of formula VI, for example 5-bromo-[1,7]naphthyridin-8-yl)-di-carbamic acid tert-butyl ester, a compound of formula $R^3B(OH)_2$, for example 3-pyridineboronic acid, sodium carbonate and ethanol are added and the mixture stirred at 80° C. for about 16 hrs to obtain a compound of formula VII. Furthermore, compound VII, for example 5-pyridin-3-yl-[1,7]naphthyridin-8-yl)-di-carbamic acid tert-butyl ester, is N-deprotected, for example, by dissolving it in ethyl acetate and by adding HCl in ethanol. The reaction mixture is stirred for about 2 hrs at room temperature to obtain a compound of formula II.

The desired compound of formula I can be prepared as follows: The compound of formula II and a compound of formula $R^2Br$, for example 2-bromo-6-methylpyridine, are dissolved in dry dioxane. 4,5-Bis(diphenylphosphino)-9,9-dimethylxanthene, cesium carbonate and tri(dibenzylideneacetone)dipalladium chloroform complex are added, and the reaction mixture is stirred for about 20 hrs at 130° C. to obtain a compound of formula I, wherein the substituents $R^1$, $R^2$ and $R^3$ are as described above.

In more detail, the compounds of formula I can be prepared as follows:

In accordance with Scheme 2, the compounds of formula III can be prepared as follows:

The compound of formula VIII (either commercially available or prepared from compounds of formula X as depicted in scheme 3 when $R^1$ is Cl and $R^3$ is H) was suspended in phosphorus oxychloride and stirred for about 5 hours at about 90° C. to obtain a compound of formula III. The desired compound of formula I can be prepared as follows: The compound of formula III and a compound of formula $R^2NH_2$, for example 2-amnio-4-methylthiazole are dissolved in dry dioxane. 4,5-Bis(diphenylphosphino)-9,9-dimethylxanthene, cesium carbonate and tri(dibenzylideneacetone)dipalladium chloroform complex are added and the reaction mixture is stirred for about 20 hrs at about 130° C. to obtain a compound of formula I.

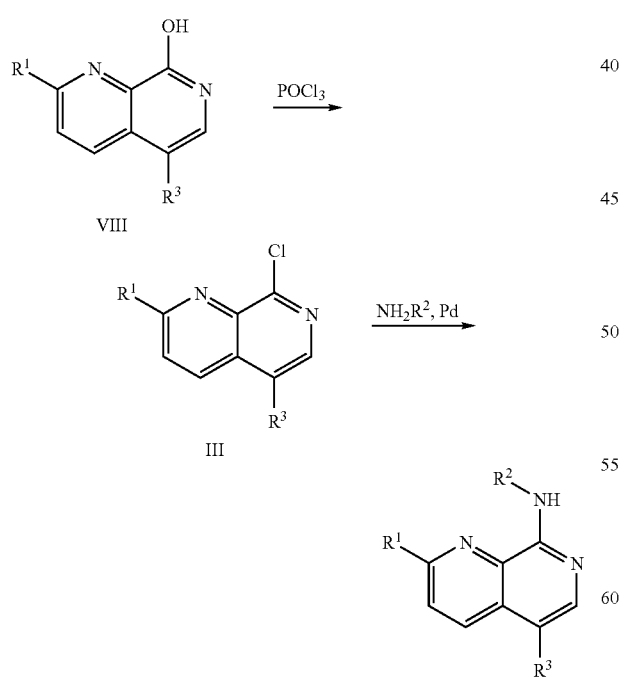

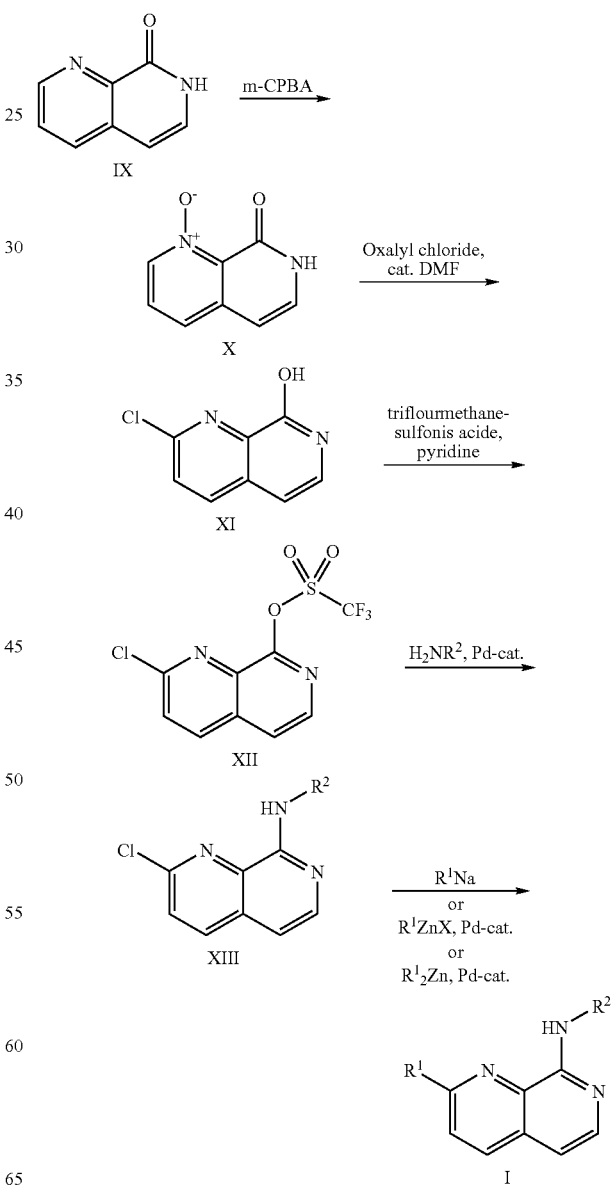

wherein the substituents $R^1$, $R^2$ and $R^3$ are as described above.

wherein the substituents $R^1$ and $R^2$ are as described above.

In more detail, the compounds of formula I can be prepared as follows:

In accordance with Scheme 3, the compound of formula X, 1-oxy-7H-[1,7]naphthyridin-8-one can be prepared as follows: The compound of formula IX, 7H-[1,7]naphthyridin-8-one (which can be prepared from commercially available starting product in accordance with literature *Chemical & Pharmaceutical Bullentin* (1985), 33(2), 626-33) was stirred for about 70 hours at room temperature in chloroform with 3-chloroperbenzoic acid to obtain the compound of formula X. To a suspension of 1-oxy-7H-[1,7]naphthyridin-8-one in dry N,N-dimethylformamide was added drop wise oxalyl chloride at 0° C. After completed addition, the mixture was allowed to warm to room temperature and stirred for about 30 minutes to obtain the compound of formula XI, 2-chloro-[1,7]naphthyridin-8-ol. To a solution of 2-chloro-[1,7]naphthyridin-8-ol in pyridine was added trifluoromethanesulfonic anhydride at about −10° C. The reaction mixture was allowed to warm to room temperature and stirred for about 1 hour to obtain the compound of formula XII, trifluoro-methanesulfonic acid 2-chloro-[1,7]naphthyridin-8-yl ester. Furthermore, the compound of formula XII and a compound of formula $R^2NH_2$, for example 2-amnio-4-methylthiazole are dissolved in dry dioxane. 4,5-Bis(diphenylphosphino)-9,9-dimethylxanthene, cesium carbonate and tri(dibenzylidene-acetone)dipalladium chloroform complex are added and the reaction mixture is stirred for about 20 hrs at about 130° C. to obtain a compound of formula XIII. The desired compound of formula I can be prepared as follows: To a compound of formula XIII in dry tetrahydrofuran were added tetrakis(triphenylphosphine)palladium and a about 1.0 M solution of diethylzinc in n-hexane. The reaction mixture was heated at reflux for about 1 hour to obtain a compound of formula I.

Pharmaceutically acceptable salts of compounds of formula I can be manufactured readily according to methods known per se and taking into consideration the nature of the compound to be converted into a salt. Inorganic or organic acids such as, for example, hydrochloric acid, hydrobromic acid, sulphuric acid, nitric acid, phosphoric acid or citric acid, formic acid, fumaric acid, maleic acid, acetic acid, succinic acid, tartaric acid, methanesulphonic acid, p-toluenesulphonic acid and the like are suitable for the formation of pharmaceutically acceptable salts of basic compounds of formula I. Compounds which contain the alkali metals or alkaline earth metals, for example sodium, potassium, calcium, magnesium or the like, basic amines or basic amino acids are suitable for the formation of pharmaceutically acceptable salts of acidic compounds.

The compounds of formula I and their pharmaceutically acceptable salts are, as already mentioned above, metabotropic glutamate receptor antagonists and can be used for the treatment or prevention of mGluR5 receptor mediated disorders, such as acute or chronic pain, urinary incontinence, liver damage or failure whether drug or disease induced, obesity or Fragile-X or autism, acute, traumatic and chronic degenerative processes of the nervous system, such as Alzheimer's disease, senile dementia, Parkinson's disease, Huntington's chorea, amyotrophic lateral sclerosis and multiple sclerosis, psychiatric diseases such as schizophrenia and anxiety, depression and drug dependency as shown in "*European Journal of Pharmacology* (2004), 497(1), 25-27.", "*Journal of Hepatology* (2003), 38(2), 179-187" and "*Hepatology (Philadelphia)* (2000), 31(3), 649-655".

The compounds of formula I and their pharmaceutically acceptable salts are especially useful as analgesics. Treatable kinds of pain include inflammatory pain such as arthritis and rheumatoid disease, vasculitis, neuropathic pain such as trigeminal or herpetic neuralgia, diabetic neuropathy pain, causalgia, hyperalgesia, severe chronic pain, post-operative pain and pain associated with various conditions like cancer, angina, renal or billiay colic, menstruation, migraine and gout.

The pharmacological activity of the compounds was tested using the following method: For binding experiments, cDNA encoding human mGlu 5a receptor was transiently transfected into EBNA cells using a procedure described by Schlaeger and Christensen [Cytotechnology 15:1-13 (1998)]. Cell membrane homogenates were stored at −80° C. until the day of assay where upon they were thawed and resuspended and polytronised in 15 mM Tris-HCl, 120 mM NaCl, 100 mM KCl, 25 mM $CaCl_2$, 25 mM $MgCl_2$ binding buffer at pH 7.4 to a final assay concentration of 20 μg protein/well.

Saturation isotherms were determined by addition of twelve [$^3$H]MPEP concentrations (0.04-100 nM) to these membranes (in a total volume of 200 μl) for 1 h at 4° C. Competition experiments were performed with a fixed concentration of [$^3$H]MPEP (2 nM) and $IC_{50}$ values of test compounds evaluated using 11 concentrations (0.3-10,000 nM). Incubations were performed for 1 h at 4° C.

At the end of the incubation, membranes were filtered onto unifilter (96-well white microplate with bonded GF/C filter preincubated 1 h in 0.1% PEI in wash buffer, Packard BioScience, Meriden, Conn.) with a Filtermate 96 harvester (Packard BioScience) and washed 3 times with cold 50 mM Tris-HCl, pH 7.4 buffer. Nonspecific binding was measured in the presence of 10 μM MPEP. The radioactivity on the filter was counted (3 min) on a Packard Top-count microplate scintillation counter with quenching correction after addition of 45 μl of microscint 40 (Canberra Packard S.A., Zürich, Switzerland) and shaking for 20 min.

For functional assays, [$Ca^{2+}$]i measurements were performed as described previously by Porter et al. [Br. J. Pharmacol. 128:13-20 (1999)]on recombinant human mGlu 5a receptors in HEK-293 cells. The cells were dye loaded using Fluo 4-AM (obtainable by FLUKA, 0.2 μM final concentration). [$Ca^{2+}$]i measurements were performed using a fluorometric imaging plate reader (FLIPR, Molecular Devices Corporation, La Jolla, Calif., USA). Antagonist evaluation was performed following a 5 min preincubation with the test compounds followed by the addition of a submaximal addition of agonist.

The inhibition (antagonists) curves were fitted with a four parameter logistic equation giving $IC_{50}$, and Hill coefficient using iterative non linear curve fitting software (Xcel fit).

For binding experiments the Ki values of the compounds tested are given. The Ki value is defined by the following formula:

$$K_i = IC_{50}/[1+L/K_d]$$

in which the $IC_{50}$ values are those concentrations of the compounds tested which cause 50% inhibition of the competing radioligand ([$^3$H]MPEP). L is the concentration of radioligand used in the binding experiment and the $K_d$ value of the radioligand is empirically determined for each batch of membranes prepared.

The compounds of the present invention are mGluR 5a receptor antagonists. The activities of compounds of formula I as measured in the assay described above and as presented in the table hereafter in the range of $K_i$<200 nM.

| Example | Ki (nM) |
|---------|---------|
| 1 | 25 |
| 2 | 89 |
| 5 | 62 |
| 6 | 33 |
| 7 | 18 |
| 8 | 38 |
| 9 | 86 |
| 10 | 19 |
| 11 | 8 |
| 12 | 56 |
| 14 | 66 |
| 15 | 66 |
| 17 | 41 |
| 18 | 41 |
| 19 | 44 |
| 42 | 56 |
| 43 | 51 |
| 68 | 38 |
| 81 | 51 |

The present invention also provides pharmaceutical compositions containing compounds of formula I or pharmaceutically acceptable salts thereof and a pharmaceutically acceptable carrier. Such pharmaceutical compositions can be in the form of tablets, coated tablets, dragées, hard and soft gelatin capsules, solutions, emulsions or suspensions. The pharmaceutical compositions also can be in the form of suppositories or injectable solutions.

The pharmaceutical compositions of the invention, in addition to one or more compounds of the invention, contain a pharmaceutically acceptable carrier. Suitable pharmaceutically acceptable carriers include pharmaceutically inert, inorganic or organic carriers. Lactose, corn starch or derivatives thereof, talc, stearic acid or its salts and the like can be used, for example, as such as carriers for tablets, coated tablets, dragées and hard gelatin capsules. Suitable carriers for soft gelatin capsules are, for example, vegetable oils, waxes, fats, semi-solid and liquid polyols and the like; depending on the nature of the active substance no carriers are, however, usually required in the case of soft gelatin capsules. Suitable carriers for the production of solutions and syrups are, for example, water, polyols, sucrose, invert sugar, glucose and the like. Adjuvants, such as alcohols, polyols, glycerol, vegetable oils and the like, can be used for aqueous injection solutions of water-soluble salts of compounds of formula I, but as a rule are not necessary. Suitable carriers for suppositories are, for example, natural or hardened oils, waxes, fats, semi-liquid or liquid polyols and the like.

In addition, the pharmaceutical compositions can contain preservatives, solubilizers, stabilizers, wetting agents, emulsifiers, sweeteners, colorants, flavorants, salts for varying the osmotic pressure, buffers, masking agents or antioxidants. They can also contain still other therapeutically valuable substances.

The present invention also provides a method for the manufacture of pharmaceutical compositions. Such process comprises bringing one or more compounds of formula I and/or pharmaceutically acceptable acid addition salts thereof and, if desired, one or more other therapeutically valuable substances into a galenical administration form together with one or more therapeutically inert carriers.

The compounds and compositions of the present invention can be administered in a conventional manner, for example, orally, rectally, or parenterally. The pharmaceutical compositions of the invention can be administered orally, for example, in the form of tablets, coated tablets, dragées, hard and soft gelatin capsules, solutions, emulsions, or suspensions. The pharmaceutical compositions also can be administered rectally, for example, in the form of suppositories, or parenterally, for example, in the form of injection solutions.

Compounds of formula I are metabotropic glutamate receptor antagonists. Compounds of formula I are distinguished by having valuable therapeutic properties. They can be used in the treatment or prevention of mGluR5 receptor mediated disorders. Such disorders include acute and/or chronic neurological disorders, in particular acute or chronic pain, urinary incontinence, gastrointestinal reflux disorder, liver damage or failure whether drug or disease induced, obesity or Fragile-X or autism, acute, traumatic and chronic degenerative processes of the nervous system, such as Alzheimer's disease, senile dementia, Parkinson's disease, Huntington's chorea, amyotrophic lateral sclerosis and multiple sclerosis, psychiatric diseases such as schizophrenia and anxiety, depression and drug dependency.

The dosage at which compounds of the invention can be administered can vary within wide limits and will, of course, be fitted to the individual requirements in each particular case. In general, the effective dosage for oral or parenteral administration is between 0.01-20 mg/kg/day, with a dosage of 0.1-10 mg/kg/day being preferred for all of the indications described. The daily dosage for an adult human being weighing 70 kg accordingly lies between 0.7-1400 mg per day, preferably between 7 and 700 mg per day.

The following examples are provided to further elucidate the invention.

EXAMPLE 1

(6-Methyl-pyridin-2-yl)-[1,7]naphthyridin-8-yl-amine

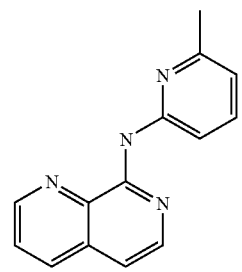

8-Chloro-[1,7]naphthyridine (Example A) (0.2 g, 1.2 mmol) and 2-amino-6-methylpyridine (0.13 g, 1.2 mmol) were dissolved in 8 ml dry dioxane. 4,5-bis(diphenylphosphino)-9,9-dimethylxanthene (145 mg, 0.24 mmol), cesium carbonate (0.63 g, 1.95 mmol) and tri(dibenzylideneacetone)dipalladium chloroform complex (0.13 g, 0.12 mmol) were added and the reaction mixture was stirred under microwave irradiation for 50 minutes at 150° C. The reaction mixture was then evaporated and purified by flash chromatography on silica gel (heptane/ethyl acetate 95:5->70:30 gradient). The desired product was obtained as a light yellow solid (98 mg, 34%), MS: m/e=237.1 (M+H$^+$).

EXAMPLE 2

(3-Chloro-phenyl)-[1,7]naphthyridin-8-yl-amine

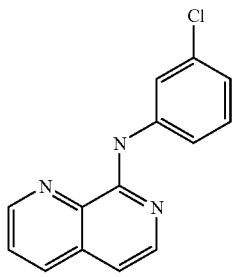

The title compound, MS: m/e=256.0 (M+H$^+$), was prepared in accordance with the general method of example 1 from 8-chloro-[1,7]naphthyridine and 3-chloroaniline.

EXAMPLE 3

(5-Fluoro-pyridin-2-yl)-[1,7]naphthyridin-8-yl-amine

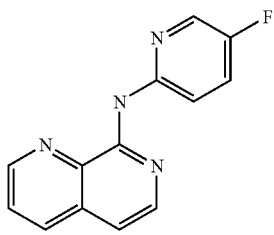

The title compound, MS: m/e=241.2 (M+H$^+$), was prepared in accordance with the general method of example 1 from 8-chloro-[1,7]naphthyridine and 2-amino-5-fluoropyridine.

EXAMPLE 4

[1,7]Naphthyridin-8-yl-pyrimidin-4-yl-amine

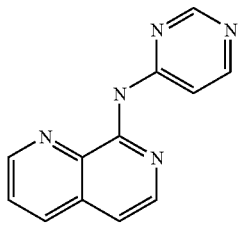

The title compound, MS: m/e=224.3 (M+H$^+$), was prepared in accordance with the general method of example 1 from 8-chloro-[1,7]naphthyridine and 2-aminopyrimidine.

EXAMPLE 5

(4-Methyl-thiazol-2-yl)-[1,7]naphthyridin-8-yl-amine

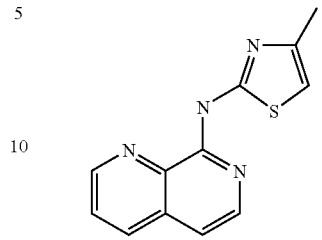

The title compound, MS: m/e=243.3 (M+H$^+$), was prepared in accordance with the general method of example 1 from 8-chloro-[1,7]naphthyridine and 2-amino-4-methylthiazole.

EXAMPLE 6

(6-Methyl-pyridin-2-yl)-(5-pyridin-3-yl-[1,7]naphthyridin-8-yl)-amine

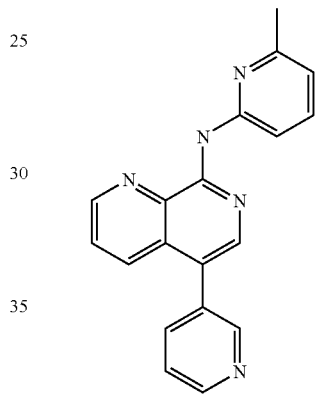

Step 1: (5-Pyridin-3-yl-1,71 naphthyridin-8-yl)-di-carbamic acid tert-butyl ester Tetrakis(triphenylphosphine)palladium(0) (570 mg, 0.5 mmol) was dissolved in 200 ml toluene. (5-Bromo-[1,7] naphthyridin-8-yl)-di-carbamic acid tert-butyl ester (4.2 g, 10 mmol) (Example B), 3-pyridineboronic acid (1.46 g, 11.9 mmol), 2M sodium carbonate (29.7 ml, 59 mmol) and 50 ml ethanol were added and the mixture stirred at 80° C. for 16 hrs. The reaction mixture was extracted with water and two times ethyl acetate. The organic extracts were washed with water and brine, dried with sodium sulfate, filtered and evaporated. The crude product was purified by flash chromatography on silica gel (heptane/ethyl acetate 1:1->0:100 gradient). The desired compound was obtained as a light yellow solid (4.1 g, 98%), MS: m/e=423.3 (M+H+).

Step 2: 5-Pyridin-3-yl-[1,7]naphthyridin-8-ylamine (5-Pyridin-3-yl-[1,7]naphthyridin-8-yl)-di-carbamic acid tert-butyl ester (4.1 g, 9.7 mmol) was dissolved in 10 ml ethyl acetate and 8M HCl in ethanol (48.5 ml, 380 mmol) was added. The reaction mixture was stirred for 2 hrs at room temperature. The reaction mixture was evaporated and extracted carefully with sat. NaHCO$_3$— solution and two times ethyl acetate. The combined organic extracts were washed with brine, dried with sodium sulfate, filtered and evaporated. The desired compound was obtained as a yellow solid (2.06 g, 96%), MS: m/e=223.2 (M+H$^+$).

Step 3: (6-Methyl-pyridin-2-yl)-(5-pyridin-3-yl-[1,7]naphthyridin-8-yl)-amine

5-Pyridin-3-yl-[1,7]naphthyridin-8-ylamine (0.1 g, 0.45 mmol) and 2-bromo-6-methylpyridine (0.14 g, 0.8 mmol) were dissolved in 4 ml dry dioxane. 4,5-bis(diphenylphosphino)-9,9-dimethylxanthene (52 mg, 0.09 mmol), cesium carbonate (0.23 g, 0.72 mmol) and tri(dibenzylideneacetone) dipalladium chloroform complex (47 mg, 0.045 mmol) were added and the reaction mixture was stirred for 20 hrs at 130° C. The reaction mixture was then evaporated and purified by flash chromatography on silica gel (heptane/ethyl acetate 1:1->0:100 gradient). The desired product was obtained as a light yellow solid (66 mg, 47%), MS: m/e=314.0 (M+H$^+$).

EXAMPLE 7

(3-Chloro-phenyl)-(5-pyridin-3-yl-[1,7]naphthyridin-8-yl)-amine

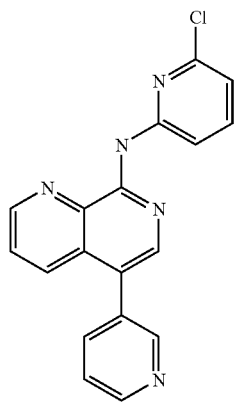

The title compound, MS: m/e=333.1 (M+H$^+$), was prepared in accordance with the general method of example 6 step 3 from 5-pyridin-3-yl-[1,7]naphthyridin-8-ylamine and 1-chloro-3-iodobenzene.

EXAMPLE 8

(2-Chloro-pyridin-4-yl)-(5-pyridin-3-yl-[1,7]naphthyridin-8-yl)-amine

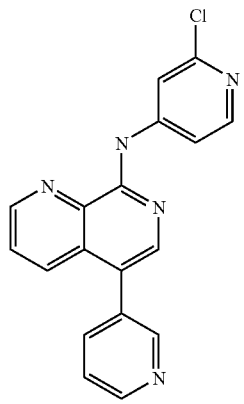

The title compound, MS: m/e=334.2 (M+H$^+$), was prepared in accordance with the general method of example 6 step 3 from 5-pyridin-3-yl-[1,7]naphthyridin-8-ylamine and 2-chloro-4-iodopyridine.

EXAMPLE 9

(5-Methyl-pyridin-2-yl)-(5-pyridin-3-yl-[1,7]naphthyridin-8-yl)-amine

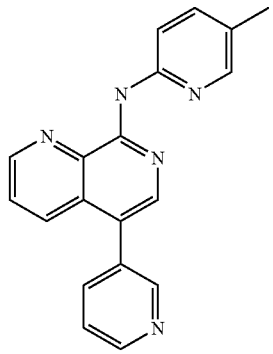

The title compound, MS: m/e=314.0 (M+H$^+$), was prepared in accordance with the general method of example 6 step 3 from 5-pyridin-3-yl-[1,7]naphthyridin-8-ylamine and 2-bromo-5-methylpyridine.

EXAMPLE 10

(5-Fluoro-pyridin-2-yl)-(5-pyridin-3-yl-[1,7]naphthyridin-8-yl)-amine

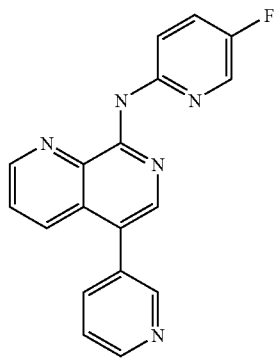

The title compound, MS: m/e=318.1 (M+H$^+$), was prepared in accordance with the general method of example 6 step 3 from 5-pyridin-3-yl-[1,7]naphthyridin-8-ylamine and 2-bromo-5-fluoro-pyridine (Example C).

EXAMPLE 11

(3-Chloro-phenyl)-[5-(6-chloro-pyridin-3-yl)-[1,7]naphthyridin-8-yl]-amine

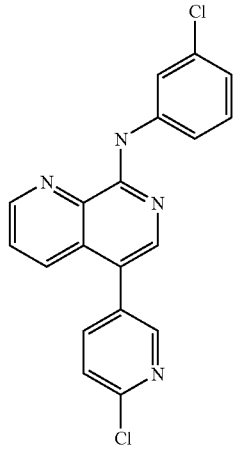

The title compound, MS: m/e=367.0 (M+H⁺), was prepared in accordance with the general method of example 6 step 1, step 2 and step 3 from (5-bromo-[1,7]naphthyridin-8-yl)-di-carbamic acid tert-butyl ester (Example B), 4-chloro-3-pyridineboronic acid and 1-chloro-3-iodobenzene.

EXAMPLE 12

(2-Chloro-pyridin-4-yl)-[5-(6-methoxy-pyridin-3-yl)-[1,7]naphthyridin-8-yl]-amine

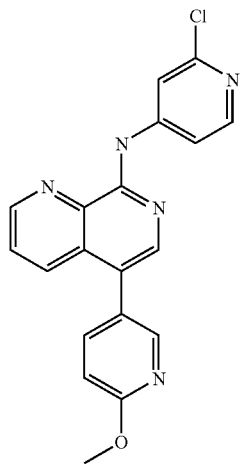

The title compound, MS: m/e=364.1 (M+H⁺), was prepared in accordance with the general method of example 6 step 1, step 2 and step 3 from (5-bromo-[1,7]naphthyridin-8-yl)-di-carbamic acid tert-butyl ester (Example B), 2-methoxy-5-pyridineboronic acid and 4-iodo-2-chloropyridine.

EXAMPLE 13

(5-Fluoro-pyridin-2-yl)-[5-(6-methoxy-pyridin-3-yl)-[1,7]naphthyridin-8-yl]-amine

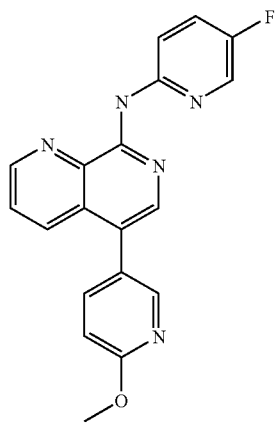

The title compound, MS: m/e=348.3 (M+H⁺), was prepared in accordance with the general method of example 6 step 1, step 2 and step 3 from (5-bromo-[1,7]naphthyridin-8-yl)-di-carbamic acid tert-butyl ester (Example B), 2-methoxy-5-pyridineboronic acid and 2-bromo-5-fluoro-pyridine (Example C).

EXAMPLE 14

(2-Chloro-pyridin-4-yl)-[5-(5-fluoro-pyridin-3-yl)-[1,7]naphthyridin-8-yl]-amine

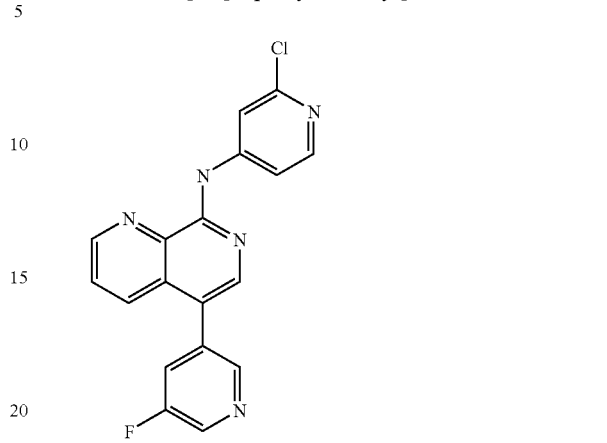

The title compound, MS: m/e=352.3 (M+H⁺), was prepared in accordance with the general method of example 6 step 1, step 2 and step 3 from (5-bromo-[1,7]naphthyridin-8-yl)-di-carbamic acid tert-butyl ester (Example B), 2-methoxy-5-pyridineboronic acid and 4-iodo-2-chloropyridine.

EXAMPLE 15

(5-Fluoro-pyridin-2-yl)-[5-(5-fluoro-pyridin-3-yl)-[1,7]naphthyridin-8-yl]-amine

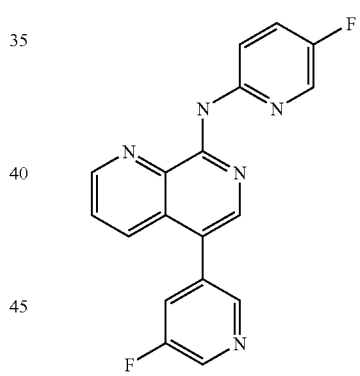

Step 1: [5-(5-Fluoro-pyridin-3-yl)-[1,7]naphthyridin-8-yl]-di-carbamic acid tert-butyl ester Tetrakis(triphenylphosphine)palladium(0) (147 mg, 0.13 mmol) was dissolved in 56 ml toluene. [5-(4,4,5,5-Tetramethyl-[1,3,2]dioxaborolan-2-yl)-[1,7]naphthyridin-8-yl]-di-carbamic acid tert-butyl ester (1.2 g, 2.55 mmol) (Example D), 5-bromo-3-fluoropyridine (0.58 g, 3.3 mmol), 2M sodium carbonate (7.64 ml, 7.6 mmol) and 14 ml ethanol were added and the mixture stirred at 80° C. for 16 hrs. The reaction mixture was extracted with water and two times ethyl acetate. The organic extracts were washed with water and brine, dried with sodium sulfate, filtered and evaporated. The crude product was purified by flash chromatography on silica gel (heptane/ethyl acetate 100:0->50:50 gradient). The desired compound was obtained as a light brown solid (0.76 g, 68%), MS: m/e=441.3 (M+H+).

Step 2: 5-(5-Fluoro-pyridin-3-yl)-[1,7]naphthyridin-8-ylamine

[5-(5-Fluoro-pyridin-3-yl)-[1,7]naphthyridin-8-yl]-dicarbamic acid tert-butyl ester (0.74 g, 1.7 mmol) was dissolved in 2 ml ethyl acetate and 8M HCl in ethanol (12.6 ml, 101 mmol) was added. The reaction mixture was stirred for 3.5 hrs at room temperature. The reaction mixture was evaporated and washed carefully with sat. NaHCO₃— solution and two times ethyl acetate. The combined organic extracts were extracted with brine, dried with sodium sulfate, filtered and evaporated. The desired compound was obtained as an orange solid (0.32 g, 80%), MS: m/e=241.3 (M+H⁺).

Step 3: (5-Fluoro-pyridin-2-yl)-[5-(5-fluoro-pyridin-3-yl)-[1,7]naphthyridin-8-yl]-amine 5-(5-Fluoro-pyridin-3-yl)-[1,7]naphthyridin-8-ylamine (0.1 g, 0.42 mmol) and 2-bromo-5-fluoropyridine (0.13 g, 0.76 mmol) (Example C) were dissolved in 3 ml dry dioxane. 4,5-bis(diphenylphosphino)-9,9-dimethylxanthene (48 mg, 0.084 mmol), cesium carbonate (0.22 g, 0.67 mmol) and tri(dibenzylideneacetone)dipalladium chloroform complex (43 mg, 0.042 mmol) were added and the reaction mixture was stirred for 20 hrs at 130° C. The reaction mixture was then evaporated and purified by flash chromatography on silica gel (heptane/ethyl acetate 95:5->30:70 gradient). The desired product was obtained as a light red solid (35 mg, 25%), MS: m/e=336.3 (M+H⁺).

EXAMPLE 16

5-[8-(3-Chloro-phenylamino)-[1,7]naphthyridin-5-yl]-nicotinic acid ethyl ester

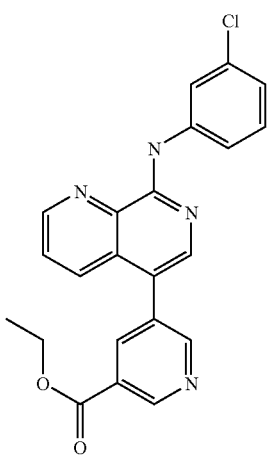

The title compound, MS: m/e=405.3 (M+H⁺), was isolated as a byproduct of the reaction from [5-(4,4,5,5-tetramethyl-[1,3,2]dioxaborolan-2-yl)-[1,7]naphthyridin-8-yl]-di-carbamic acid tert-butyl ester (Example D), 5-bromonicotinonitrile and 1-chloro-3-iodobenzene prepared in accordance with the general method of example 15 step 1, step 2 and step 3.

EXAMPLE 17

(5-Fluoro-pyridin-2-yl)-[5-(5-methoxy-pyridin-3-yl)-[1,7]naphthyridin-8-yl]-amine

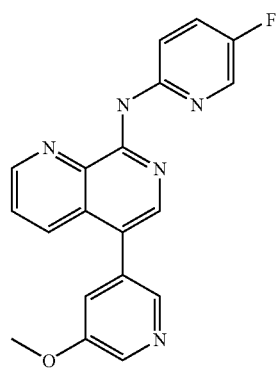

The title compound, MS: m/e=348.4 (M+H⁺), was prepared in accordance with the general method of example 15 step 1, step 2 and step 3 from [5-(4,4,5,5-tetramethyl-[1,3,2]dioxaborolan-2-yl)-[1,7]naphthyridin-8-yl]-di-carbamic acid tert-butyl ester (Example D), 5-bromo-3-methoxypyridine and 2-bromo-5-fluoropyridine (Example C).

EXAMPLE 18

(2-Chloro-pyridin-4-yl)-(5-pyrimidin-5-yl-[1,7]naphthyridin-8-yl)-amine

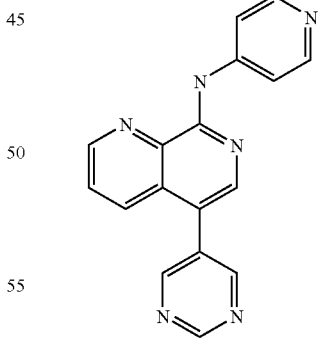

The title compound, MS: m/e=335.2 (M+H⁺), was prepared in accordance with the general method of example 15 step 1, step 2 and step 3 from [5-(4,4,5,5-tetramethyl-[1,3,2]dioxaborolan-2-yl)-[1,7]naphthyridin-8-yl]-di-carbamic acid tert-butyl ester (Example D), 5-bromopyrimidine and 4-iodo-2-chloropyridine.

EXAMPLE 19

(5-Fluoro-pyridin-2-yl)-(5-pyrimidin-5-yl-[1,7]naphthyridin-8-yl)-amine

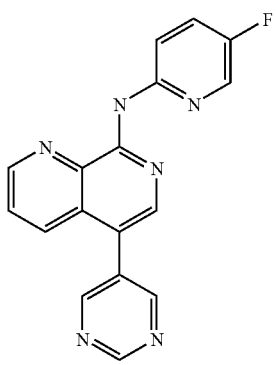

The title compound, MS: m/e=319.1 (M+H⁺), was prepared in accordance with the general method of example 15 step 1, step 2 and step 3 from [5-(4,4,5,5-tetramethyl-[1,3,2]dioxaborolan-2-yl)-[1,7]naphthyridin-8-yl]-di-carbamic acid tert-butyl ester (Example D), 5-bromopyrimidine and 2-bromo-5-fluoropyridine (Example C).

EXAMPLE 20

2-[8-(5-Fluoro-pyridin-2-ylamino)-[1,7]naphthyridin-5-yl]-benzonitrile

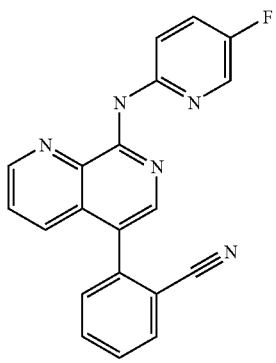

The title compound, MS: m/e=342.2 (M+H⁺), was prepared in accordance with the general method of example 15 step 1, step 2 and step 3 from [5-(4,4,5,5-tetramethyl-[1,3,2]dioxaborolan-2-yl)-[1,7]naphthyridin-8-yl]-di-carbamic acid tert-butyl ester (Example D), 2-bromobenzonitrile and 2-bromo-5-fluoropyridine (Example C).

EXAMPLE 21

(5-Chloro-pyridin-2-yl)-[5-(5-fluoro-pyridin-3-yl)-[1,7]naphthyridin-8-yl]-amine

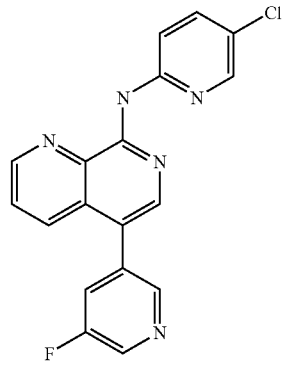

The title compound, MS: m/e=352.1 (M+H⁺), was prepared in accordance with the general method of example 15 step 3 from 5-(5-fluoro-pyridin-3-yl)-[1,7]naphthyridin-8-ylamine and 2-bromo-5-chloropyridine.

EXAMPLE 22

(2-Methyl-[1,7]naphthyridin-8-yl)-(4-methyl-thiazol-2-yl)-amine

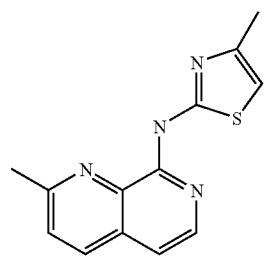

The title compound, MS: m/e=257.2 (M+H⁺), was prepared in accordance with the general method of example 1 from 8-chloro-2-methyl-[1,7]naphthyridine (Example E) and 2-amino-4-methylthiazole.

EXAMPLE 23

(5-Chloro-pyridin-2-yl)-(2-methyl-[1,7]naphthyridin-8-yl)-amine

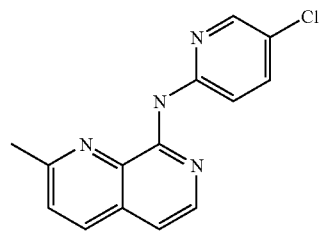

The title compound, MS: m/e=271.3 (M+H⁺), was prepared in accordance with the general method of example 1 from 8-chloro-2-methyl-[1,7]naphthyridine (Example E) and 2-amino-5-chloropyridine.

EXAMPLE 24

(5-Fluoro-pyridin-2-yl)-(2-methyl-[1,7]naphthyridin-8-yl)-amine

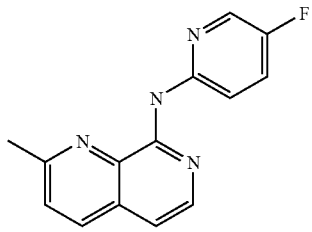

The title compound, MS: m/e=255.3 (M+H⁺), was prepared in accordance with the general method of example 1 from 8-chloro-2-methyl-[1,7]naphthyridine (Example E) and 2-amino-5-fluoropyridine.

EXAMPLE 25

(2-Chloro-pyridin-4-yl)-(2-methyl-[1,7]naphthyridin-8-yl)-amine

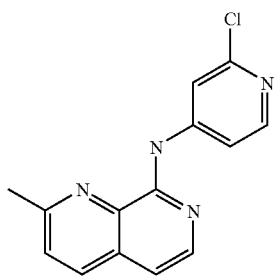

The title compound, MS: m/e=271.2 (M+H⁺), was prepared in accordance with the general method of example 1 from 8-chloro-2-methyl-[1,7]naphthyridine (Example E) and 2-chloro-4-aminopyridine.

EXAMPLE 26

(3-Chloro-phenyl)-(2-methyl-[1,7]naphthyridin-8-yl)-amine

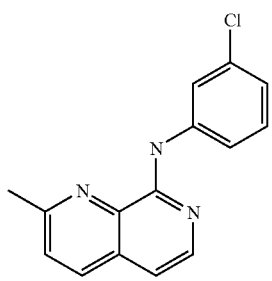

The title compound, MS: m/e=270.3/272.2 (M+H⁺), was prepared in accordance with the general method of example 1 from 8-chloro-2-methyl-[1,7]naphthyridine (Example E) and 3-chloroaniline.

EXAMPLE 27

(2-Methyl-[1,7]naphthyridin-8-yl)-(1-methyl-1H-pyrazol-3-yl)-amine

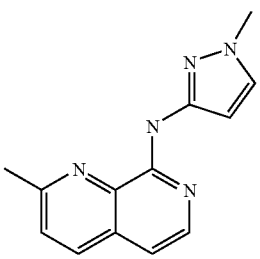

The title compound, MS: m/e=240.3 (M+H⁺), was prepared in accordance with the general method of example 1 from 8-chloro-2-methyl-[1,7]naphthyridine (Example E) and 1-methyl-1H-pyrazol-3-ylamine.

EXAMPLE 28

(2-Methyl-[1,7]naphthyridin-8-yl)-(2-methyl-thiazol-4-yl)-amine

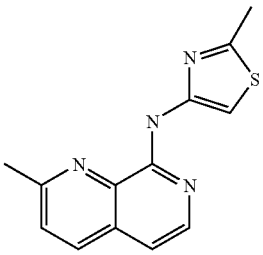

The title compound, MS: m/e=257.2 (M+H⁺), was prepared in accordance with the general method of example 1 from 8-chloro-2-methyl-[1,7]naphthyridine (Example E) and 4-amino-2-methylthiazole (Example F).

EXAMPLE 29

(2-Chloro-[1,7]naphthyridin-8-yl)-(4-methyl-thiazol-2-yl)-amine

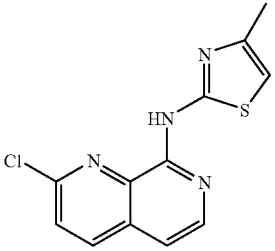

The title compound, MS: m/e=277 (M+H⁺), was prepared in accordance with the general method of example 1 from trifluoro-methanesulfonic acid 2-chloro-[1,7]naphthyridin-8-yl ester (Example G) and 2-amino-4-methylthiazole.

EXAMPLE 30

(2-Chloro-[1,7]naphthyridin-8-yl)-(2-methyl-thiazol-4-yl)-amine

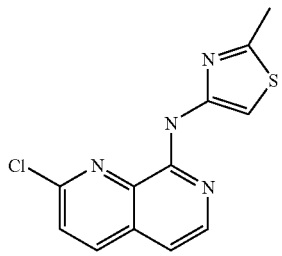

The title compound, MS: m/e=277.0/279.1 (M+H$^+$), was prepared in accordance with the general method of example 1 from trifluoro-methanesulfonic acid 2-chloro-[1,7]naphthyridin-8-yl ester (Example G) and 4-amino-2-methylthiazole (Example F).

EXAMPLE 31

(2-Methoxy-[1,7]naphthyridin-8-yl)-(4-methyl-thiazol-2-yl)-amine

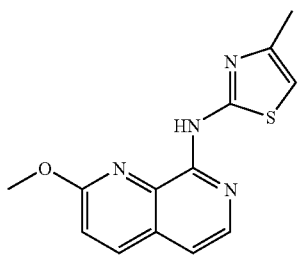

To a solution of (2-chloro-[1,7]naphthyridin-8-yl)-(4-methyl-thiazol-2-yl)-amine (0.055 g, 0.20 mmol) in 1.5 ml sulfolane was added g sodium methylate (0.55, 1.0 mmol). The reaction mixture was heated for 10 min at 100° C. under microwave irradiation. The reaction mixture was diluted with water and extracted with three portions of methyl-tert.-butyl ether. The combined organic layers were washed with two portions of water, dried over sodium sulfate and concentrated to dryness. Flash-chromatography gave the title compound (0.043 g, 79%) as an off-white solid, MS m/e (%): 273 (M+H$^+$, 100).

EXAMPLE 32

(2-Ethyl-[1,7]naphthyridin-8-yl)-(4-methyl-thiazol-2-yl)-amine

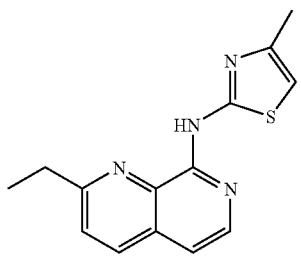

To a solution of (2-chloro-[1,7]naphthyridin-8-yl)-(4-methyl-thiazol-2-yl)-amine (0.055 g, 0.20 mmol) in 2 ml dry tetrahydrofuran (purged with argon) were subsequently added tetrakis(triphenylphosphine)palladium (0.011 g, 0.0095 mmol) and a 1.0 M solution of diethylzinc in n-hexane (0.4 ml, 0.4 mmol). The reaction mixture was heated at reflux for 1 h. Cooling to room temperature was followed by quenching with saturated aqueous ammonium chloride solution at 0-5° C. The aquous layer was basified to pH 12 with 1 M aqueous sodium hydroxide solution and extracted with three portions of methyl-tert.-butyl ether. The combined organic layers were washed with brine, dried over sodium sulfate and concentrated to dryness. Flash-chromatography gave the title compound (0.015 g, 28%) as light yellow solid, MS m/e (%): 271 (M+H$^+$, 100).

EXAMPLE 33

(4-Methyl-thiazol-2-yl)-(5-pyrimidin-5-yl-[1,7]naphthyridin-8-yl)-amine

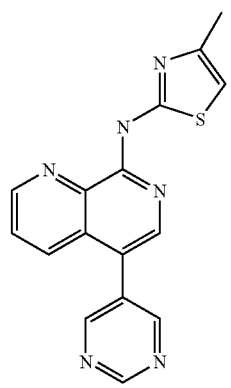

The title compound, MS: m/e=321.2 (M+H$^+$), was prepared in accordance with the general method of example 15 step 1 and step 3 from 5-bromo-8-chloro-[1,7]naphthyridine (Example H), 5-pyrimidineboronic acid and 2-amino-4-methylthiazole.

EXAMPLE 34

(4-Methyl-thiazol-2-yl)-(5-pyridin-3-yl-[1,7]naphthyridin-8-yl)-amine

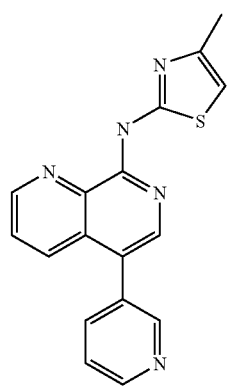

The title compound, MS: m/e=320.0 (M+H$^+$), was prepared in accordance with the general method of example 15 step 1 and step 3 from 5-bromo-8-chloro-[1,7]naphthyridine (Example H), 5-pyridineboronic acid and 2-amino-4-methylthiazole.

EXAMPLE 35

(1-Methyl-1H-pyrazol-3-yl)-(5-pyridin-3-yl-[1,7]naphthyridin-8-yl)-amine

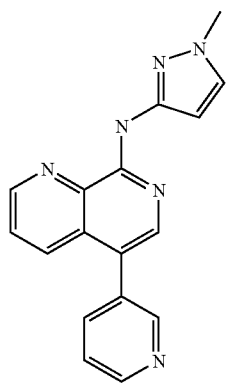

The title compound, MS: m/e=303.2 (M+H$^+$), was prepared in accordance with the general method of example 15 step 1 and step 3 from 5-bromo-8-chloro-[1,7]naphthyridine (Example H), 5-pyridineboronic acid and 1-methyl-1H-pyrazol-3-ylamine.

EXAMPLE 36

(2-Methyl-thiazol-4-yl)-(5-pyridin-3-yl-[1,7]naphthyridin-8-yl)-amine

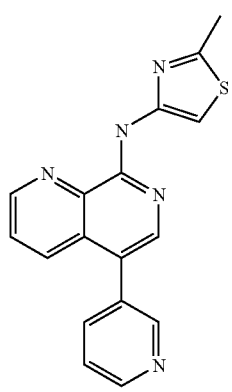

The title compound, MS: m/e=320.2 (M+H$^+$), was prepared in accordance with the general method of example 15 step 1 and step 3 from 5-bromo-8-chloro-[1,7]naphthyridine (Example H), 5-pyridineboronic acid and 4-amino-2-methylthiazole (Example F).

EXAMPLE 37

(2-Methyl-thiazol-4-yl)-(5-pyrimidin-5-yl-[1,7]naphthyridin-8-yl)-amine

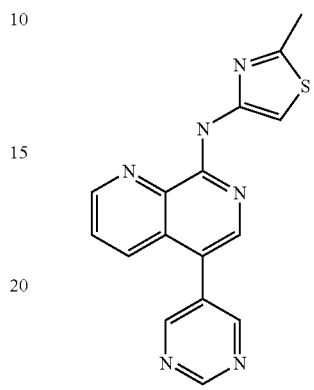

The title compound, MS: m/e=321.2 (M+H$^+$), was prepared in accordance with the general method of example 15 step 1 and step 3 from 5-bromo-8-chloro-[1,7]naphthyridine (Example H), 5-pyrimidineboronic acid and 4-amino-2-methylthiazole (Example F).

EXAMPLE 38

(2-Methyl-5-pyridin-3-yl-[1,7]naphthyridin-8-yl)-(4-methyl-thiazol-2-yl)-amine

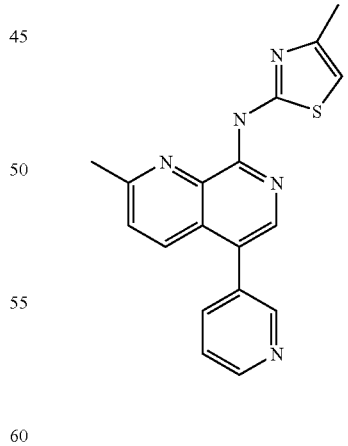

The title compound, MS: m/e=334.2 (M+H$^+$), was prepared in accordance with the general method of example 15 step 1 and step 3 from 8-chloro-5-iodo-2-methyl-[1,7]naphthyridine (Example I), 3-pyridineboronic acid and 2-amino-4-methylthiazole.

EXAMPLE 39

(5-Fluoro-pyridin-2-yl)-(2-methyl-5-pyridin-3-yl-[1,7]naphthyridin-8-yl)-amine

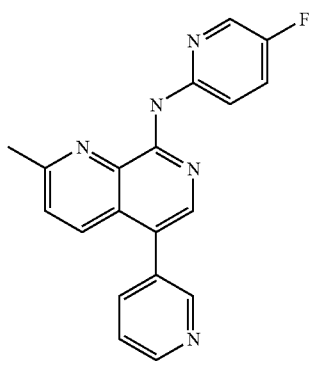

The title compound, MS: m/e=332.2 (M+H$^+$), was prepared in accordance with the general method of example 15 step 1 and step 3 from 8-chloro-5-iodo-2-methyl-[1,7]naphthyridine (Example I), 3-pyridineboronic acid and 2-amino-5-fluoropyridine.

EXAMPLE 40

(2-Methyl-5-pyridin-3-yl-[1,7]naphthyridin-8-yl)-(2-methyl-thiazol-4-yl)-amine

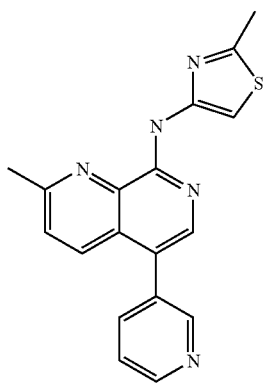

The title compound, MS: m/e=334.2 (M+H$^+$), was prepared in accordance with the general method of example 15 step 1 and step 3 from 8-chloro-5-iodo-2-methyl-[1,7]naphthyridine (Example I), 3-pyridineboronic acid and 4-amino-2-methylthiazole (Example F).

EXAMPLE 41

(2-Chloro-pyridin-4-yl)-(2-methyl-5-pyridin-3-yl-[1,7]naphthyridin-8-yl)-amine

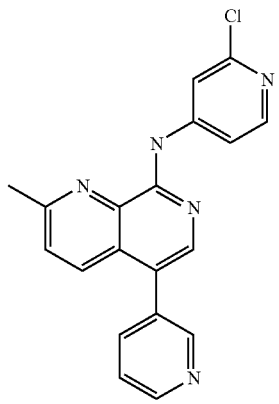

The title compound, MS: m/e=348.2/350.2 (M+H$^+$), was prepared in accordance with the general method of example 15 step 1 and step 3 from 8-chloro-5-iodo-2-methyl-[1,7]naphthyridine (Example I), 3-pyridineboronic acid and 2-chloro-4-aminopyridine.

EXAMPLE 42

[5-(3-Methoxy-phenyl)-2-methyl-[1,7]naphthyridin-8-yl]-(4-methyl-thiazol-2-yl)-amine

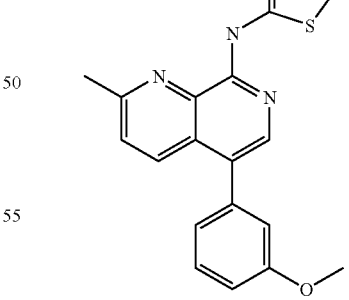

The title compound, MS: m/e=363.2 (M+H$^+$), was prepared in accordance with the general method of example 15 step 1 and step 3 from 8-chloro-5-iodo-2-methyl-[1,7]naphthyridine (Example I), 3-methoxyphenylboronic acid and 2-amino-4-methylthiazole.

EXAMPLE 43

(4-Methyl-thiazol-2-yl)-[2-methyl-5-(3-trifluoromethyl-phenyl)-[1,7]naphthyridin-8-yl]-amine

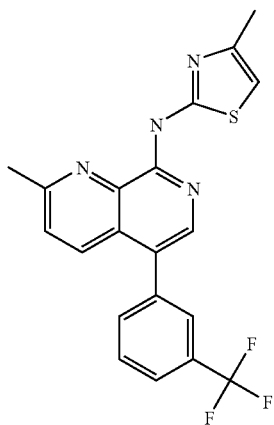

The title compound, MS: m/e=401.2 (M+H$^+$), was prepared in accordance with the general method of example 15 step 1 and step 3 from 8-chloro-5-iodo-2-methyl-[1,7]naphthyridine (Example I), 3-(trifluoromethyl)phenylboronic acid and 2-amino-4-methylthiazole.

EXAMPLE 44

(2-Methyl-5-pyrimidin-5-yl-[1,7]naphthyridin-8-yl)-(2-methyl-thiazol-4-yl)-amine

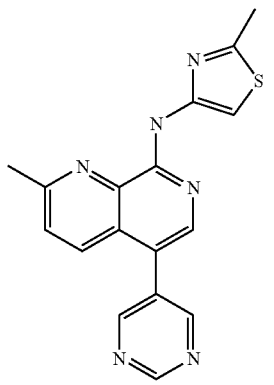

The title compound, MS: m/e=335.2 (M+H$^+$), was prepared in accordance with the general method of example 15 step 1 and step 3 from 8-chloro-5-iodo-2-methyl-[1,7]naphthyridine (Example I), 5-pyrimidineboronic acid and 4-amino-2-methylthiazole (Example F).

EXAMPLE 45

[5-(6-Chloro-pyridin-3-yl)-2-methyl-[1,7]naphthyridin-8-yl]-(2-methyl-thiazol-4-yl)-amine

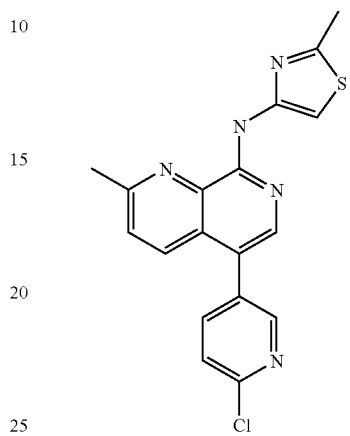

The title compound, MS: m/e=368.0 (M+H$^+$), was prepared in accordance with the general method of example 15 step 1 and step 3 from 8-chloro-5-iodo-2-methyl-[1,7]naphthyridine (Example I), 2-chloro-5-pyridineboronic acid and 4-amino-2-methylthiazole (Example F).

EXAMPLE 46

[5-(6-Chloro-pyridin-3-yl)-2-methyl-[1,7]naphthyridin-8-yl]-(4-methyl-thiazol-2-yl)-amine

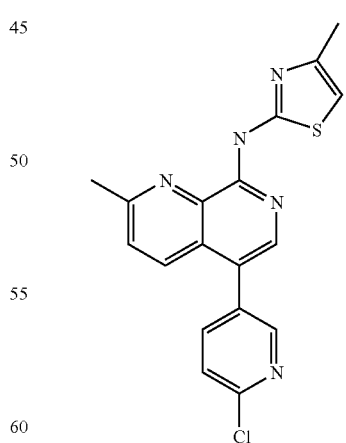

The title compound, MS: m/e=368.1 (M+H$^+$), was prepared in accordance with the general method of example 15 step 1 and step 3 from 8-chloro-5-iodo-2-methyl-[1,7]naphthyridine (Example I), 2-chloro-5-pyridineboronic acid and 2-amino-4-methylthiazole.

EXAMPLE 47

[5-(3,5-Dimethyl-isoxazol-4-yl)-2-methyl-[1,7]naphthyridin-8-yl]-(4-methyl-thiazol-2-yl)-amine

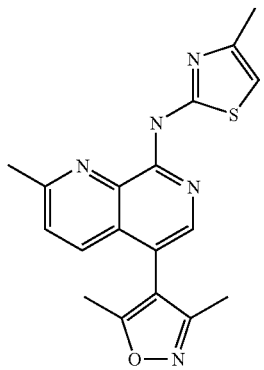

The title compound, MS: m/e=352.3 (M+H⁺), was prepared in accordance with the general method of example 15 step 1 and step 3 from 8-chloro-5-iodo-2-methyl-[1,7]naphthyridine (Example I), 3,5-dimethyl-isoxazole-4-boronic acid and 2-amino-4-methylthiazole.

EXAMPLE 48

[5-(2,5-Dimethyl-2H-pyrazol-3-yl)-2-methyl-[1,7]naphthyridin-8-yl]-(4-methyl-thiazol-2-yl)-amine

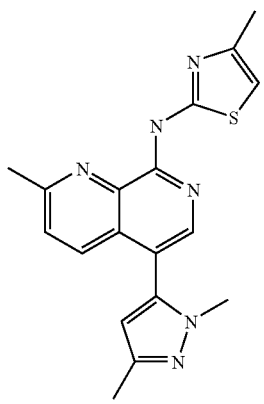

The title compound, MS: m/e=351.3 (M+H⁺), was prepared in accordance with the general method of example 15 step 1 and step 3 from 8-chloro-5-iodo-2-methyl-[1,7]naphthyridine (Example I), 1,3-dimethyl-1H-pyrazole-5-boronic acid (Example J) and 2-amino-4-methylthiazole.

EXAMPLE 49

5-[2-Methyl-8-(4-methyl-thiazol-2-ylamino)-[1,7]naphthyridin-5-yl]-pyridine-2-carbonitrile

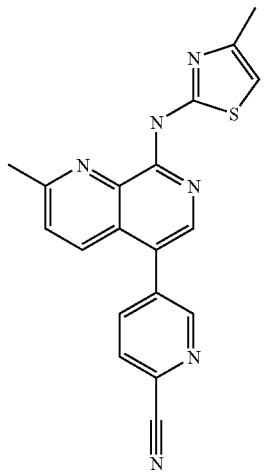

The title compound, MS: m/e=359.1 (M+H⁺), was prepared in accordance with the general method of example 15 step 1 and step 3 from 8-chloro-5-iodo-2-methyl-[1,7]naphthyridine (Example I), 2-cyanopyridine-5-boronic acid pinacol ester and 2-amino-4-methylthiazole.

EXAMPLE 50

[5-(3-Methanesulfonyl-phenyl)-2-methyl-[1,7]naphthyridin-8-yl]-(4-methyl-thiazol-2-yl)-amine

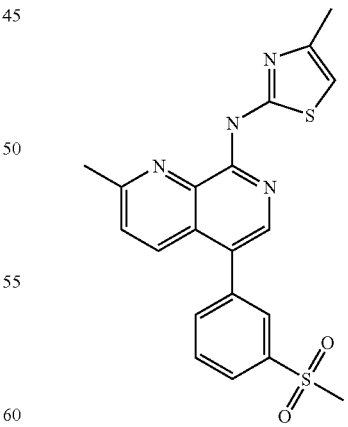

The title compound, MS: m/e=411.1 (M+H⁺), was prepared in accordance with the general method of example 15 step 1 and step 3 from 8-chloro-5-iodo-2-methyl-[1,7]naphthyridine (Example I), (3-methylsulfonylphenyl)boronic acid and 2-amino-4-methylthiazole.

EXAMPLE 51

(2-Methyl-5-pyrimidin-5-yl-[1,7]naphthyridin-8-yl)-(4-methyl-thiazol-2-yl)-amine

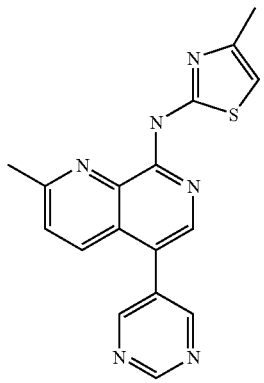

The title compound, MS: m/e=335.2 (M+H⁺), was prepared in accordance with the general method of example 15 step 1 and step 3 from 8-chloro-5-iodo-2-methyl-[1,7]naphthyridine (Example I), 5-pyrimidineboronic acid and 2-amino-4-methylthiazole.

EXAMPLE 52

(2-Methyl-5-pyridin-4-yl-[1,7]naphthyridin-8-yl)-(4-methyl-thiazol-2-yl)-amine

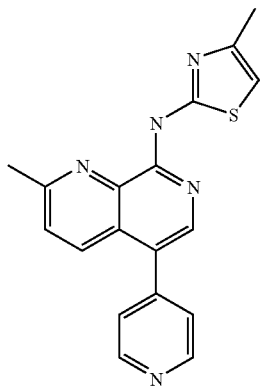

The title compound, MS: m/e=334.1 (M+H⁺), was prepared in accordance with the general method of example 15 step 1 and step 3 from 8-chloro-5-iodo-2-methyl-[1,7]naphthyridine (Example I), 4-pyridineboronic acid and 2-amino-4-methylthiazole.

EXAMPLE 53

[2-Methyl-5-(4-methyl-pyridin-3-yl)-[1,7]naphthyridin-8-yl]-(4-methyl-thiazol-2-yl)-amine

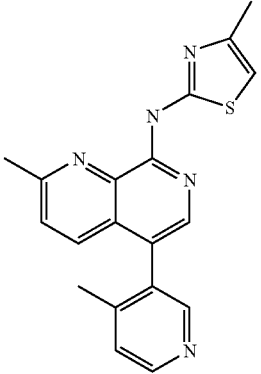

The title compound, MS: m/e=348.1 (M+H⁺), was prepared in accordance with the general method of example 15 step 1 and step 3 from 8-chloro-5-iodo-2-methyl-[1,7]naphthyridine (Example I), 4-methylpyridine-3-boronic acid and 2-amino-4-methylthiazole.

EXAMPLE 54

[5-(6-Fluoro-pyridin-3-yl)-2-methyl-[1,7]naphthyridin-8-yl]-(4-methyl-thiazol-2-yl)-amine

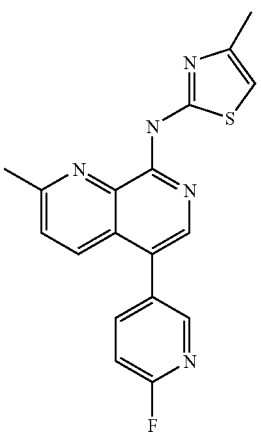

The title compound, MS: m/e=352.1 (M+H⁺), was prepared in accordance with the general method of example 15 step 1 and step 3 from 8-chloro-5-iodo-2-methyl-[1,7]naphthyridine (Example I), 2-fluoropyridine-5-boronic acid and 2-amino-4-methylthiazole.

EXAMPLE 55

[5-(6-Methoxy-pyridin-3-yl)-2-methyl-[1,7]naphthyridin-8-yl]-(4-methyl-thiazol-2-yl)-amine

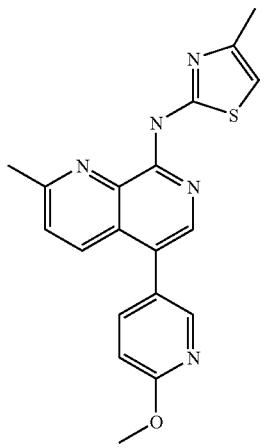

The title compound, MS: m/e=364.1 (M+H⁺), was prepared in accordance with the general method of example 15 step 1 and step 3 from 8-chloro-5-iodo-2-methyl-[1,7]naphthyridine (Example I), 2-methoxypyridine-5-boronic acid and 2-amino-4-methylthiazole.

EXAMPLE 56

[5-(5-Methoxy-pyridin-3-yl)-2-methyl-[1,7]naphthyridin-8-yl]-(4-methyl-thiazol-2-yl)-amine

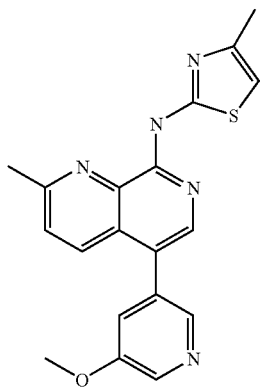

The title compound, MS: m/e=364.1 (M+H⁺), was prepared in accordance with the general method of example 15 step 1 and step 3 from 8-chloro-5-iodo-2-methyl-[1,7]naphthyridine (Example I), 3-methoxy-5-pyridineboronic acid pinacol ester and 2-amino-4-methylthiazole.

EXAMPLE 57

[2-Methyl-5-(3-methyl-pyridin-2-yl)-[1,7]naphthyridin-8-yl]-(4-methyl-thiazol-2-yl)-amine

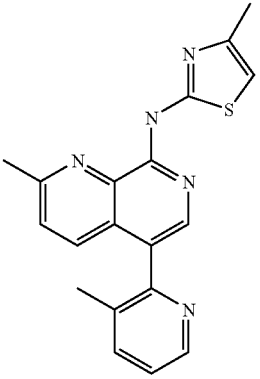

The title compound, MS: m/e=348.2 (M+H⁺), was prepared in accordance with the general method of example 15 step 1 and step 3 from 8-chloro-5-iodo-2-methyl-[1,7]naphthyridine (Example I), 3-methylpyridine-2-boronic acid and 2-amino-4-methylthiazole.

EXAMPLE 58

(2-Methyl-5-pyrimidin-5-yl-[1,7]naphthyridin-8-yl)-(4-trifluoromethyl-thiazol-2-yl)-amine

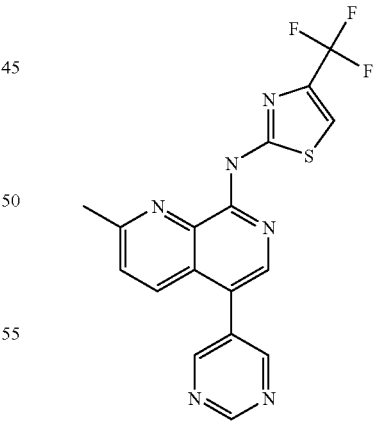

The title compound, MS: m/e=389.2 (M+H⁺), was prepared in accordance with the general method of example 15 step 1 and step 3 from 8-chloro-5-iodo-2-methyl-[1,7]naphthyridine (Example I), 5-pyrimidineboronic acid and 2-amino-4-(trifluoromethyl)thiazole.

EXAMPLE 59

(4-Chloro-thiazol-2-yl)-(2-methyl-5-pyrimidin-5-yl-[1,7]naphthyridin-8-yl)-amine

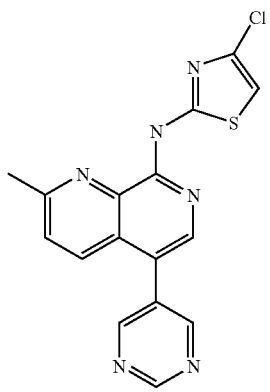

The title compound, MS: m/e=354.9 (M+H⁺), was prepared in accordance with the general method of example 15 step 1 and step 3 from 8-chloro-5-iodo-2-methyl-[1,7]naphthyridine (Example I), 5-pyrimidineboronic acid and 2-amino-4-chlorothiazole (Example K).

EXAMPLE 60

[5-(5-Fluoro-pyridin-3-yl)-2-methyl-[1,7]naphthyridin-8-yl]-(4-methyl-thiazol-2-yl)-amine

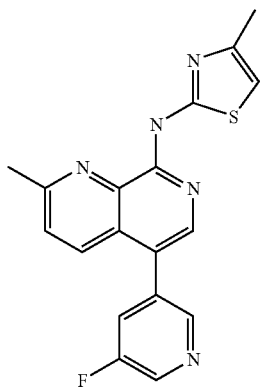

The title compound, MS: m/e=352.2 (M+H⁺), was prepared in accordance with the general method of example 15 step 1 and step 3 from 8-chloro-5-iodo-2-methyl-[1,7]naphthyridine (Example I), 3-fluoro-5-pyridineboronic acid and 2-amino-4-methylthiazole.

EXAMPLE 61

[2-Methyl-5-(6-methyl-pyridin-3-yl)-[1,7]naphthyridin-8-yl]-(4-methyl-thiazol-2-yl)-amine

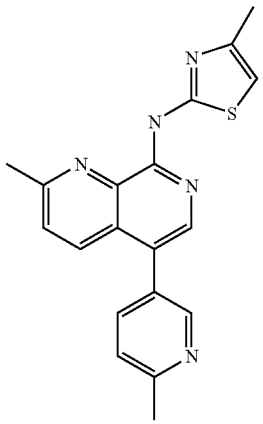

The title compound, MS: m/e=348.2 (M+H⁺), was prepared in accordance with the general method of example 15 step 1 and step 3 from 8-chloro-5-iodo-2-methyl-[1,7]naphthyridine (Example I), 2-methylpyridine-5-boronic acid hydrate and 2-amino-4-methylthiazole.

EXAMPLE 62

(2-Methyl-pyrimidin-4-yl)-(2-methyl-5-pyrimidin-5-yl-[1,7]naphthyridin-8-yl)-amine

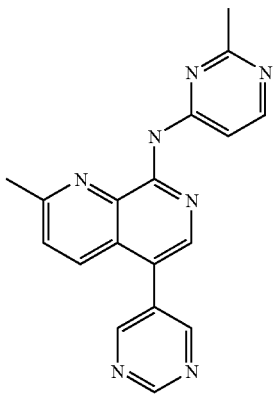

The title compound, MS: m/e=330.1 (M+H⁺), was prepared in accordance with the general method of example 15 step 1 and step 3 from 8-chloro-5-iodo-2-methyl-[1,7]naphthyridine (Example I), 5-pyrimidineboronic acid and 4-amino-2-methylpyrimidine.

EXAMPLE 63

(2-Chloro-pyridin-4-yl)-(2-methyl-5-pyrimidin-5-yl-[1,7]naphthyridin-8-yl)-amine

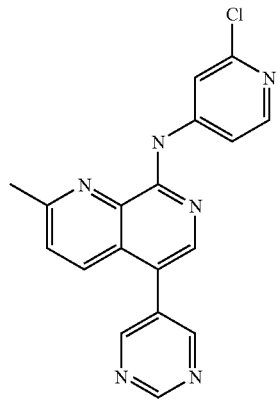

The title compound, MS: m/e=349.2 (M+H$^+$), was prepared in accordance with the general method of example 15 step 1 and step 3 from 8-chloro-5-iodo-2-methyl-[1,7]naphthyridine (Example I), 5-pyrimidineboronic acid and 4-amino-2-chloropyridine.

EXAMPLE 64

[5-(2,5-Dimethyl-2H-pyrazol-3-yl)-2-methyl-[1,7]naphthyridin-8-yl]-(2-methyl-thiazol-4-yl)-amine

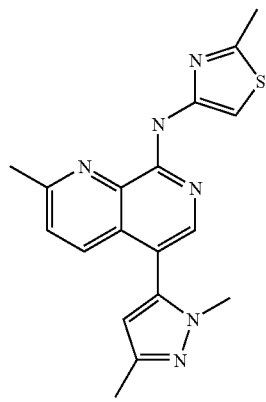

The title compound, MS: m/e=351.2 (M+H$^+$), was prepared in accordance with the general method of example 15 step 1 and step 3 from 8-chloro-5-iodo-2-methyl-[1,7]naphthyridine (Example I), 1,3-dimethyl-1H-pyrazole-5-boronic acid (Example J) and 4-amino-2-methylthiazole (Example F).

EXAMPLE 65

(2-Methyl-5-pyrimidin-2-yl-[1,7]naphthyridin-8-yl)-(2-methyl-thiazol-4-yl)-amine

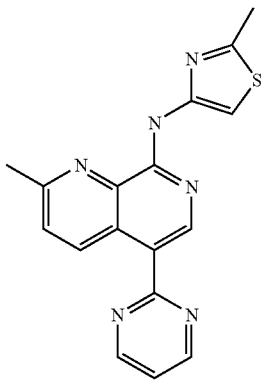

The title compound, MS: m/e=335.2 (M+H$^+$), was prepared in accordance with the general method of example 15 step 1 and step 3 from 8-chloro-2-methyl-[1,7]naphthyridine-5-boronic acid (Example L), 2-bromopyrimidine and 4-amino-2-methylthiazole (Example F).

EXAMPLE 66

[2-Methyl-5-(2-methyl-pyridin-3-yl)-[1,7]naphthyridin-8-yl]-(2-methyl-thiazol-4-yl)-amine

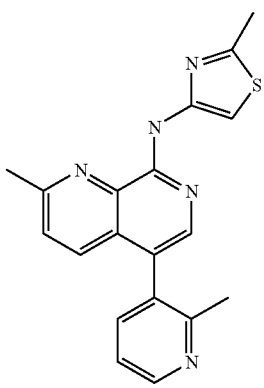

The title compound, MS: m/e=348.2 (M+H$^+$), was prepared in accordance with the general method of example 15 step 1 and step 3 from 8-chloro-2-methyl-[1,7]naphthyridine-5-boronic acid (Example L), 3-bromo-2-methylpyridine and 4-amino-2-methylthiazole (Example F).

EXAMPLE 67

(1-Methyl-1H-pyrazol-3-yl)-(2-methyl-5-pyrimidin-5-yl-[1,7]naphthyridin-8-yl)-amine

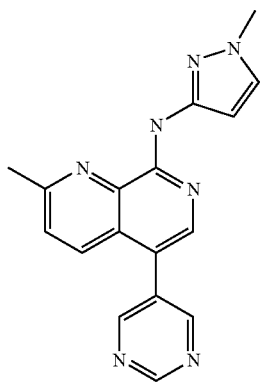

The title compound, MS: m/e=318.2 (M+H⁺), was prepared in accordance with the general method of example 15 step 1 and step 3 from 8-chloro-5-iodo-2-methyl-[1,7]naphthyridine (Example I), 5-pyrimidineboronic acid and 1-methyl-1H-pyrazol-3-ylamine.

EXAMPLE 68

[5-(3-Fluoro-phenyl)-2-methyl-[1,7]naphthyridin-8-yl]-(1-methyl-1H-pyrazol-3-yl)-amine

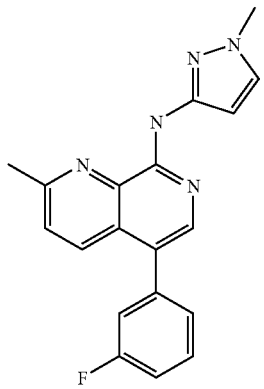

The title compound, MS: m/e=334.2 (M+H⁺), was prepared in accordance with the general method of example 15 step 1 and step 3 from 8-chloro-5-iodo-2-methyl-[1,7]naphthyridine (Example I), 3-fluorophenylboronic acid and 1-methyl-1H-pyrazol-3-ylamine.

EXAMPLE 69

[5-(5-Fluoro-pyridin-3-yl)-2-methyl-[1,7]naphthyridin-8-yl]-(1-methyl-1H-pyrazol-3-yl)-amine

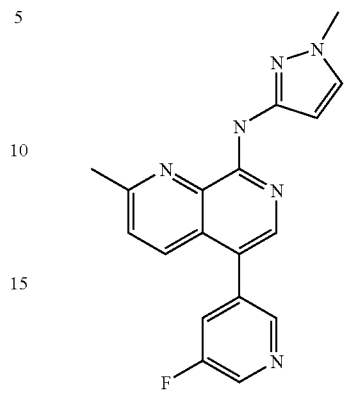

The title compound, MS: m/e=335.2 (M+H⁺), was prepared in accordance with the general method of example 15 step 1 and step 3 from 8-chloro-5-iodo-2-methyl-[1,7]naphthyridine (Example I), 3-fluoropyridine-5-boronic acid and 1-methyl-1H-pyrazol-3-ylamine.

EXAMPLE 70

[2-Methyl-5-(6-methyl-pyridin-2-yl)-[1,7]naphthyridin-8-yl]-(2-methyl-thiazol-4-yl)-amine

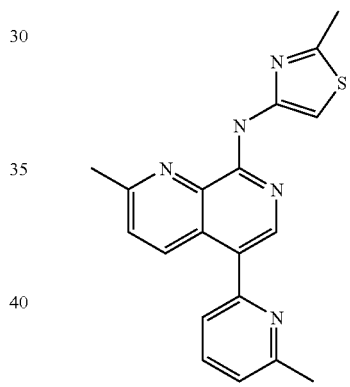

The title compound, MS: m/e=348.2 (M+H⁺), was prepared in accordance with the general method of example 15 step 1 and step 3 from 8-chloro-2-methyl-[1,7]naphthyridine-5-boronic acid (Example L), 2-bromo-6-methylpyridine and 4-amino-2-methylthiazole (Example F).

EXAMPLE 71

(4-Methyl-thiazol-2-yl)-(2-methyl-5-thiazol-2-yl-[1,7]naphthyridin-8-yl)-amine

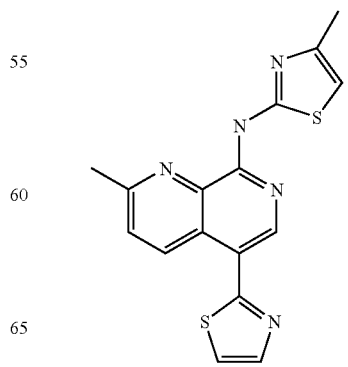

The title compound, MS: m/e=340.0 (M+H$^+$), was prepared in accordance with the general method of example 15 step 1 and step 3 from 8-chloro-2-methyl-[1,7]naphthyridine-5-boronic acid (Example L), 2-bromothiazole and 2-amino-4-methylthiazole.

EXAMPLE 72

[2-Methyl-5-(3-methyl-3H-imidazol-4-yl)-[1,7]naphthyridin-8-yl]-(4-methyl-thiazol-2-yl)-amine

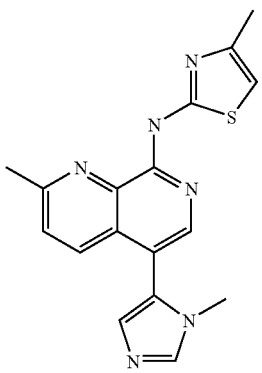

The title compound, MS: m/e=337.3 (M+H$^+$), was prepared in accordance with the general method of example 15 step 1 and step 3 from 8-chloro-2-methyl-[1,7]naphthyridine-5-boronic acid (Example L), 5-bromo-1-methyl-1H-imidazole and 2-amino-4-methylthiazole.

EXAMPLE 73

[2-Methyl-5-(3-methyl-3H-imidazol-4-yl)-[1,7]naphthyridin-8-yl]-(2-methyl-thiazol-4-yl)-amine

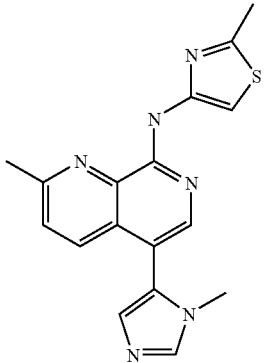

The title compound, MS: m/e=337.3 (M+H$^+$), was prepared in accordance with the general method of example 15 step 1 and step 3 from 8-chloro-2-methyl-[1,7]naphthyridine-5-boronic acid (Example L), 5-bromo-1-methyl-1H-imidazole and 4-amino-2-methylthiazole (Example F).

EXAMPLE 74

[2-Methyl-5-(3-methyl-[1,2,4]thiadiazol-5-yl)-[1,7]naphthyridin-8-yl]-(2-methyl-thiazol-4-yl)-amine

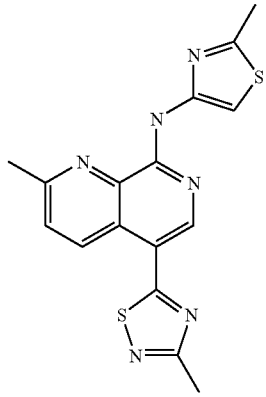

The title compound, MS: m/e=355.2 (M+H$^+$), was prepared in accordance with the general method of example 15 step 1 and step 3 from 8-chloro-2-methyl-[1,7]naphthyridine-5-boronic acid (Example L), 5-bromo-3-methyl-[1,2,4]thiadiazole (Example M) and 4-amino-2-methylthiazole (Example F).

EXAMPLE 75

[2-Methyl-5-(2-methyl-pyrimidin-5-yl)-[1,7]naphthyridin-8-yl]-(2-methyl-thiazol-4-yl)-amine

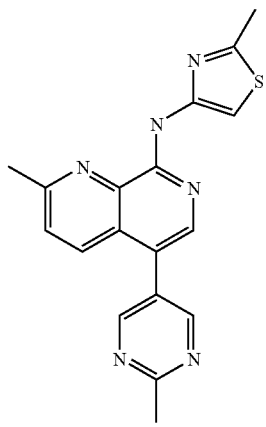

The title compound, MS: m/e=349.2 (M+H$^+$), was prepared in accordance with the general method of example 15 step 1 and step 3 from 8-chloro-2-methyl-[1,7]naphthyridine-5-boronic acid (Example L), 5-bromo-2-methylpyrimidine and 4-amino-2-methylthiazole (Example F).

EXAMPLE 76

(2-Methyl-5-pyrazin-2-yl-[1,7]naphthyridin-8-yl)-(2-methyl-thiazol-4-yl)-amine

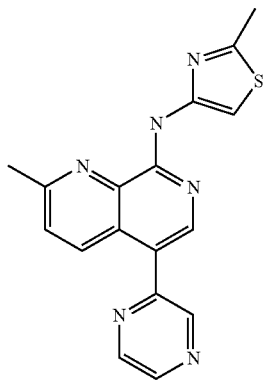

The title compound, MS: m/e=335.4 (M+H$^+$), was prepared in accordance with the general method of example 15 step 1 and step 3 from 8-chloro-2-methyl-[1,7]naphthyridine-5-boronic acid (Example L), 2-iodopyrazine and 4-amino-2-methylthiazole (Example F).

EXAMPLE 77

[5-(5-Fluoro-pyridin-3-yl)-2-methyl-[1,7]naphthyridin-8-yl]-(2-methyl-thiazol-4-yl)-amine

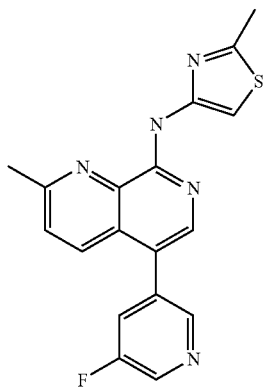

The title compound, MS: m/e=352.2 (M+H$^+$), was prepared in accordance with the general method of example 15 step 1 and step 3 from 8-chloro-5-iodo-2-methyl-[1,7]naphthyridine (Example I), 3-fluoropyridine-5-boronic acid and 4-amino-2-methylthiazole (Example F).

EXAMPLE 78

(2-Methyl-5-pyridin-3-yl-[1,7]naphthyridin-8-yl)-(4-trifluoromethyl-thiazol-2-yl)-amine

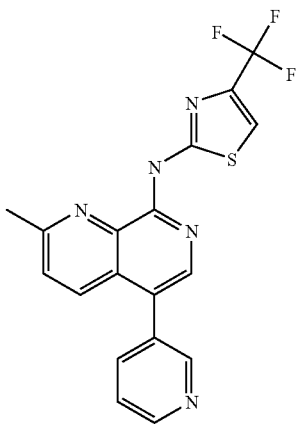

The title compound, MS: m/e=388.2 (M+H$^+$), was prepared in accordance with the general method of example 15 step 1 and step 3 from 8-chloro-5-iodo-2-methyl-[1,7]naphthyridine (Example I), 3-pyridineboronic acid and 2-amino-4-(trifluoromethyl)thiazole.

EXAMPLE 79

(4-Difluoromethyl-thiazol-2-yl)-(2-methyl-5-pyridin-3-yl-[1,7]naphthyridin-8-yl)-amine

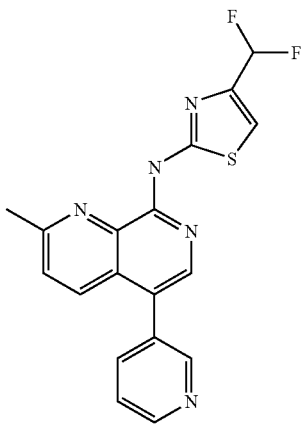

The title compound, MS: m/e=370.0 (M+H$^+$), was prepared in accordance with the general method of example 15 step 1 and step 3 from 8-chloro-5-iodo-2-methyl-[1,7]naphthyridine (Example I), 3-pyridineboronic acid and 4-amino-2-(difluoromethyl)thiazole (Example N).

EXAMPLE 80

(4-Methyl-thiazol-2-yl)-[2-methyl-5-(5-trifluoromethyl-pyridin-3-yl)-[1,7]naphthyridin-8-yl]-amine

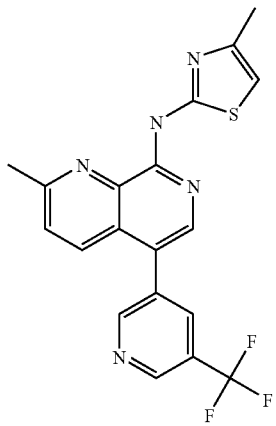

The title compound, MS: m/e=402.3 (M+H$^+$), was prepared in accordance with the general method of example 15 step 1 and step 3 from 8-chloro-2-methyl-[1,7]naphthyridine-5-boronic acid (Example L), 3-bromo-5-(trifluoromethyl)pyridine and 2-amino-4-methylthiazole.

EXAMPLE 81

(4-Methyl-thiazol-2-yl)-[2-methyl-5-(6-trifluoromethyl-pyrazin-2-yl)-[1,7]naphthyridin-8-yl]-amine

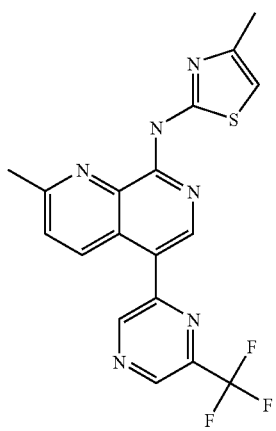

The title compound, MS: m/e=403.3 (M+H$^+$), was prepared in accordance with the general method of example 15 step 1 and step 3 from 8-chloro-2-methyl-[1,7]naphthyridine-5-boronic acid (Example L), 2-iodo-6-trifluoromethyl-pyrazine (Example O) and 2-amino-4-methylthiazole.

Synthesis of Intermediates:

EXAMPLE A

8-Chloro-[1,7]naphthyridine

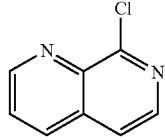

The title compound can be prepared in accordance with the preparation described in WO 2002/044189.

EXAMPLE B (5-Bromo-[1,7]naphthyridin-8-yl)-di-carbamic acid tert-butyl ester

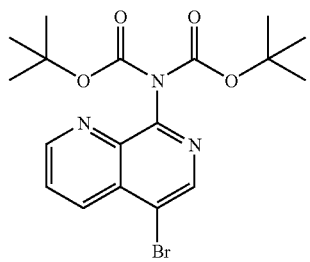

Step 1: 5-Bromo-[1,7]naphthyridin-8-ylamine

The title compound, MS: m/e=226.1 (M+H+), can be prepared in accordance with literature *Journal of Heterocyclic Chemistry* (1978), 15(5), 731-6.

Step 2:
(5-Bromo-[1,7]naphthyridin-8-yl)-di-carbamic acid tert-butyl ester

5-Bromo-[1,7]naphthyridin-8-ylamine (3.0 g, 13.4 mmol), di-tert.-butyldicarbonate (6.1 g, 28.1 mmol) and 4-(N,N-dimethylamino)pyridine (80 mg, 0.67 mmol) were dissolved in 100 ml dichloromethane and refluxed for 2 hrs. The reaction mixture was cooled and extracted with sat. NaHCO$_3$-solution and ethyl acetate. The organic extract was dried with sodium sulfate, filtered and evaporated. The crude product was purified by flash chromatography on silica gel (heptane/ethyl acetate 90:10->1:1 gradient). The desired compound was obtained as a brown solid (4.3 g, 76%), MS: m/e=426.1 (M+H$^+$).

EXAMPLE C

2-Bromo-5-fluoro-pyridine

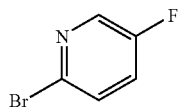

2-Amino-5-fluoropyridine (6.5 g, 58 mmol) was added in portions to cool (0-5° C.) hydrobromic acid 48% (28.8 ml, 296 mmol). Bromine (8.9 ml, 174 mmol) and a solution of sodium NaNO$_2$ (10 g, 145 mmol) in 20 ml water were added drop wise at 0-5° C. (N$_2$-evolution!). The reaction mixture was stirred for 1 hr and quenched with conc. NaOH (32%) (50.5 ml, 0.55 mol). The reaction mixture was stirred at room temperature for 20 minutes and extracted then three times with diethyl ether. The combined organic extracts were washed with brine, dried with sodium sulfate, filtered and evaporated only at 30° C. and 500 mbar (volatile!). The crude product was purified by flash chromatography on silica gel (dichloromethane/pentane 0:100->50:50 gradient). The desired compound was obtained as a light yellow solid (6.7 g, 66%).

EXAMPLE D

[5-(4,4,5,5-Tetramethyl-[1,3,2]dioxaborolan-2-yl)-[1,7]naphthyridin-8-yl]-di-carbamic acid tert-butyl ester

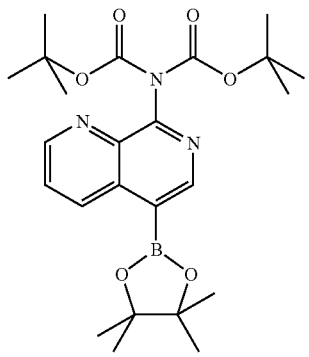

(5-Bromo-[1,7]naphthyridin-8-yl)-di-carbamic acid tert-butyl ester (19.5 g, 46 mmol) (Example B) was dissolved in 280 ml dioxane. Bis(pinacolo)diborone (18.7 g, 73.5 mmol), bis(triphenylphosiphine)palladium(II) chloride (1.94 g, 2.8 mmol) and potassium acetate (13.5 g, 138 mmol) were added and the mixture stirred at 85° C. for 16 hrs. The reaction mixture was evaporated, suspended in dichloromethane and purified by flash chromatography on silica gel (ethyl acetate/heptane 5:95->50:50 gradient). The desired compound was obtained as a yellow solid (17.1 g, 79%), MS: m/e=472.4 (M+H$^+$).

EXAMPLE E

8-Chloro-2-methyl-[1,7]naphthyridine

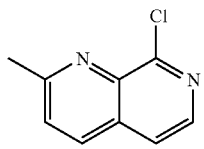

Step 1: 2-Methyl-7H-[1,7]naphthyridin-8-one

The title compound, MS: m/e=161.3 (M+H+), can be prepared in accordance with literature *Chemical & Pharmaceutical Bullentin* (1985), 33(2), 626-33 from 5-bromo-2-methylpyridine.

Step 2: 8-Chloro-2-methyl-[1,7]naphthyridine

A suspension of 2-Methyl-7H-[1,7]naphthyridin-8-one (820 mg, 5.12 mmol) and phosphorus oxychloride (7 ml, 76.8 mmol) was stirred at 90° C. for 4 hours. The reaction mixture was evaporated to dryness, poured on ice and set alkaline with aqueous ammonia. A red solution resulted. The aqueous layer was extracted with dichloromethane (three times). The combined organic layers were washed with brine, dried over Na$_2$SO$_4$ and concentrated in vacuo. The residue was purified by flash chromatography on silica gel (ethyl acetate/heptane 0:100->20:80 gradient). The desired compound was obtained as a white solid (810 mg, 89%), MS: m/e=(M+H$^+$).

EXAMPLE F

4-Amino-2-methylthiazole

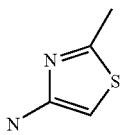

The title compound can be prepared in accordance with the preparation described in patent EP 321115.

EXAMPLE G

Trifluoro-methanesulfonic acid 2-chloro-[1,7]naphthyridin-8-yl ester

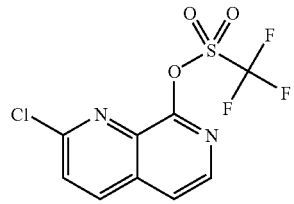

Step 1: 1-Oxy-7H-[1,7]naphthyridin-8-one

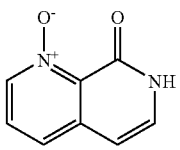

To a mixture of 7H-[1,7]naphthyridin-8-one (2.3 g, 16 mmol) (the preparation of 7H-[1,7]naphthyridin-8-one is described in Chem. Pharm. Bull. 1985, 33 (2), 626) in 100 ml chloroform was added 3-chloroperbenzoic acid (4.3 g, 70%, 17 mmol). After stirring for 70 h at room temperature and the mixture was dissolved by the addition of methanol. Aminopropyl-modified silica gel was added and the mixture was concentrated to dryness. The residue was transferred to a aminopropyl-modified silica gel column. Elution with dichloromethane/methanol gave the title compound (2.4 g, 94%) as a yellow solid, MS m/e (%)=163 (M+H$^+$, 100).

Step 2: 2-Chloro-[1,7]naphthyridin-8-ol

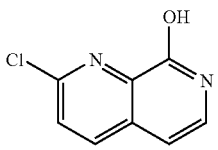

To a suspension of 1-oxy-7H-[1,7]naphthyridin-8-one (1.1 g, 6.9 mmol) in 45 ml dry N,N-dimethylformamide was added dropwise oxalyl chloride (0.77 ml, 9.0 mmol) at 0° C. After completed addition, the mixture was allowed to warm to room temperature and stirred for 30 min. Methanol was added to quench excess oxalyl chloride, and the mixture was concentrated in vacuo. The residue was redissolved in methanol and treated with aminopropyl-modified silica gel. After evaporation of the solvent the residue was transferred to a aminopropyl-modified silica gel column. Elution with dichloromethane/methanol gave the title compound (0.72 g, 57%) as a white solid, MS m/e (%)=181 (M+H$^+$, 100).

Step 3: Trifluoro-methanesulfonic acid 2-chloro-[1,7]naphthyridin-8-yl ester

To a solution of 2-chloro-[1,7]naphthyridin-8-ol (0.89 g, 4.9 mmol) in 30 ml pyridine was added trifluoromethanesulfonic anhydride (1.06 ml, 6.41 mmol) at −10° C. The reaction mixture was allowed to warm to room temperature. After 1 h the pyridine was removed by Kugelrohrdistillation. Flash chromatography gave the title compound (0.99 g, 64%) as a light brown oil, MS m/e (%): 313 (M+H$^+$, 100).

EXAMPLE H

5-Bromo-8-chloro-[1,7]naphthyridine

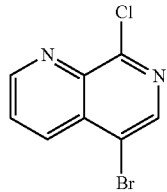

Step 1: 5-Bromo-[1,7]naphthyridin-8-ylamine

The title compound, MS: m/e=226.1 (M+H+), can be prepared in accordance with literature *Journal of Heterocyclic Chemistry* (1978), 15(5), 731-6.

Step 2: 5-Bromo-8-chloro-[1,7]naphthyridine

5-Bromo-[1,7]naphthyridin-8-ylamine (3.0 g, 13.4 mmol) was suspended in 10 ml water and 17.4 ml concentrated (25%) hydrochloric acid and cooled to 0° C. A solution of NaNO$_2$ (7.4 g, 107.2 mmol) in 5 ml water was added drop wise (N$_2$ evolution!) and stirred for 1 hour at 0° C. The reaction mixture was extracted with ethyl acetate (three times). The organic layers were dried over Na$_2$SO$_4$ and concentrated in vacuo. The residue was purified by flash chromatography on silica gel (ethyl acetate/heptane 10:90->100:0 gradient). The desired compound was obtained as a yellow solid (1.02 g, 31%), MS: m/e=245.2 (M+H$^+$).

EXAMPLE I

8-Chloro-5-iodo-2-methyl-[1,7]naphthyridine

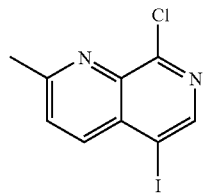

Step 1: 2-Methyl-7H-[1,7]naphthyridin-8-one

The title compound, MS: m/e=161.3 (M+H+), can be prepared in accordance with literature *Chemical & Pharmaceutical Bullentin* (1985), 33(2), 626-33 from 5-bromo-2-methylpyridine.

Step 2: 5-Iodo-2-methyl-7H-[1,7]naphthyridin-8-one

2-Methyl-7H-[1,7]naphthyridin-8-one (10.0 g, 62.4 mmol) was suspended in 300 ml acetonitrile and N-iodosuccinimide (16.9 g, 74.9 mmol) was added. The suspension was stirred for 3 hours at reflux. The reaction mixture was cooled to room temperature and filtered. The solid was washed with acetonitrile and dried for 30 minutes at 50° C. and <20 mbar, to get the desired compound as a brown solid (14.3 g, 80%), MS: m/e=287.0 (M+H$^+$).

Step 3:
8-Chloro-5-iodo-2-methyl-[1,7]naphthyridine

5-Iodo-2-methyl-7H-[1,7]naphthyridin-8-one (14.2 g, 49.8 mmol) was suspended in phosphorus oxychloride (68 ml, 750 mmol) and stirred for 5 hours at 90° C. The reaction mixture was cooled to room temperature and evaporated to dryness. The residue was taken up in dichloromethane and extracted carefully with saturated NaHCO$_3$-Solution. The aqueous layer was washed two times with dichloromethane. The organic layers were dried over MgSO$_4$ and concentrated in vacuo. The residue was purified by flash chromatography on silica gel (ethyl acetate/heptane 10:90->100:0 gradient). The desired compound was obtained as a light red solid (4.8 g, 32%), MS: m/e=305.0 (M+H$^+$).

EXAMPLE J 1,3-Dimethyl-1H-pyrazole-5-boronic acid

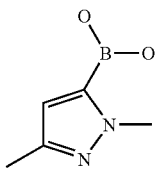

The title compound can be prepared in accordance with the preparation described in literature *Journal of Heterocyclic Chemistry* (2004), 41(6), 931-939.

EXAMPLE K

4-Chloro-thiazol-2-ylamine

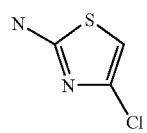

2-Chloroethyl 5-chloro-2-thiazolecarbamate (400 mg, 1.66 mmol), ammonium chloride (2.0 g, 37.3 mmol), Vitamin B12 (34 mg, 0.017 mmol) and zinc dust (activated by 0.1N HCl) (330 mg, 5.0 mmol) were stirred for 16 hours at room temperature in 10 ml ethanol and 10 ml water. The reaction mixture was filtered and extracted three times with ethyl acetate. The organic layers were dried over Na$_2$SO$_4$ and concentrated in vacuo. The desired compound was obtained as a light yellow solid (56 mg, 25%).

EXAMPLE L

8-Chloro-2-methyl-[1,7]naphthyridine-5-boronic acid

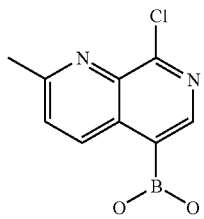

8-Chloro-5-iodo-2-methyl-[1,7]naphthyridine (Example I) (2.5 g, 8.2 mmol) and triisopropylborate (1.9 ml, 8.2 mmol) were dissolved in 80 ml THF and cooled to −75° C. n-Butyllithium (1.6M in hexane) (5.1 ml, 8.2 mmol) was added drop wise at −70° C. The reaction mixture was stirred for 1 hour at −75° C. and for 1 hour without ice-bath. 10 ml 2N HCl-solution were added and extracted three times with ethyl acetate. The organic layers were washed with brine, dried over $Na_2SO_4$ and concentrated in vacuo. The residue was crystallized in acetonitrile to get the desired compound as a red solid (1.05 g, 58%), MS: m/e=221.3 (M−H$^+$).

EXAMPLE M

5-Bromo-3-methyl-[1,2,4]thiadiazole

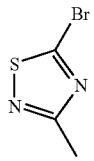

The title compound can be prepared in accordance with the general method of example C from 3-methyl-1,2,4-thiadiazol-5-amine.

EXAMPLE N

4-Amino-2-(difluoromethyl)thiazole

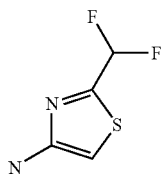

Step 1: 2-(Di-tert-butoxycarbonyl)amino-thiazole-4-carboxylic acid ethyl ester The title compound, MS: m/e=373.2 (M+H+), can be prepared in accordance with the general method of example B, step 2 from ethyl 2-amino-1,3-thiazole-4-carboxylate.

Step 2: (4-Hydroxymethyl-thiazol-2-yl)-carbamic acid tert-butyl ester 2-(Di-tert-butoxycarbonyl)amino-thiazole-4-carboxylic acid ethyl ester (8.0 g, 21.5 mmol) was dissolved in 160 ml THF and cooled to −15° C. Lithiumaluminium hydride (1M in THF) (23.5 ml, 23.6 mmol) was added drop wise and the mixture was stirred for 1 hour at −15° C. Water was added and the mixture was extracted with saturated potassium D-tartrate-solution in water and three times ethyl acetate. The organic layers were dried over $Na_2SO_4$ and concentrated in vacuo. The residue was purified by flash chromatography on silica gel (ethyl acetate/heptane 5:95->50:50 gradient). The desired compound was obtained as a light yellow solid (3.2 g, 77%), MS: m/e=231.2 (M+H$^+$).

Step 3: (4-Formyl-thiazol-2-yl)-carbamic acid tert-butyl ester (4-Hydroxymethyl-thiazol-2-yl)-carbamic acid tert-butyl ester (1.62 g, 6.95 mmol) was dissolved in 30 ml dichloromethane. Mangan(IV)oxid (3.65 g, 41.7 mmol) was added and the reaction mixture stirred at reflux for 2 hrs. The suspension was filtered through a dicalite speed plus pad and washed with dichloromethane. The solvents were evaporated and the desired compound was obtained as a light yellow solid (1.25 g, 78%), MS: m/e=229.2 (M+H$^+$).

Step 4: (2-Difluoromethyl-thiazol-4-yl)-carbamic acid tert-butyl ester

To a solution of 1.25 g (5.5 mmol) (4-formyl-thiazol-2-yl)-carbamic acid tert-butyl ester in 30 ml of dry methylene chloride were added 2.15 ml (16.4 mmol) diethylaminosulfur trifluoride (DAST). The mixture was stirred at room temperature for 16 hours. The reaction mixture was quenched with sat. $NaHCO_3$— solution and extracted with water and methylene chloride. The combined organic extracts were dried with sodium sulfate, filtered and evaporated. The crude product was purified by flash chromatography on silica gel (heptane/ethyl acetate 4:1). The desired compound was obtained as a yellow solid (810 mg, 59%), MS: m/e=251.2 (M+H$^+$).

Step 5: 4-Amino-2-(difluoromethyl)thiazole

The title compound, MS: m/e=151.1 (M+H+), can be prepared in accordance with the general method of example 6, step 2 from (2-difluoromethyl-thiazol-4-yl)-carbamic acid tert-butyl ester.

EXAMPLE O

2-Iodo-6-trifluoromethyl-pyrazine

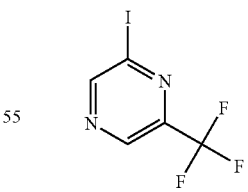

The title compound can be prepared in accordance with the preparation described in U.S. Pat. No. 5,384,408.

Preparation of the Pharmaceutical Compositions:

EXAMPLE I

Tablets of the following composition are produced in a conventional manner:

|  | mg/Tablet |
| --- | --- |
| Active ingredient | 100 |
| Powdered. lactose | 95 |
| White corn starch | 35 |
| Polyvinylpyrrolidone | 8 |
| Na carboxymethylstarch | 10 |
| Magnesium stearate | 2 |
| Tablet weight | 250 |

EXAMPLE II

Tablets of the following composition are produced in a conventional manner:

|  | mg/Tablet |
| --- | --- |
| Active ingredient | 200 |
| Powdered. lactose | 100 |
| White corn starch | 64 |
| Polyvinylpyrrolidone | 12 |
| Na carboxymethylstarch | 20 |
| Magnesium stearate | 4 |
| Tablet weight | 400 |

EXAMPLE III

Capsules of the following composition are produced:

|  | mg/Capsule |
| --- | --- |
| Active ingredient | 50 |
| Crystalline. lactose | 60 |
| Microcrystalline cellulose | 34 |
| Talc | 5 |
| Magnesium stearate | 1 |
| Capsule fill weight | 150 |

The active ingredient having a suitable particle size, the crystalline lactose and the microcrystalline cellulose are homogeneously mixed with one another, sieved and thereafter talc and magnesium stearate are admixed. The final mixture is filled into hard gelatin capsules of suitable size.

What is claimed is:

1. A compound of formula I

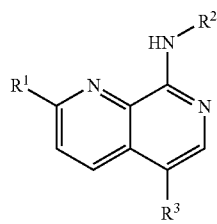

wherein $R^1$ is hydrogen, halogen, cyano, lower alkoxy, lower alkyl, lower alkyl substituted by halogen, cycloalkyl, $-(CH_2)_n-$O-lower alkyl, or $-C(O)R'$ wherein R' is lower alkyl, lower alkoxy or $NR_2$;

R is hydrogen or lower alkyl;

$R^2$ is aryl or is 5- or 6-membered heteroaryl selected from the group consisting of imidazolyl, isoxazolyl, pyrazolyl, pyridinyl, thiadiazolyl, and thiazolyl;

$R^3$ is hydrogen, OR, $NR_2$, lower alkyl, cycloalkyl, aryl, heterocycloalkyl, 5- or 6-membered heteroaryl, C(O)$NR_2$, lower alkyl substituted by halogen, or $-C(O)R'$ wherein R' is lower alkyl, lower alkoxy or $NR_2$;

wherein the aryl, cycloalkyl, heterocycloalkyl or 5- or 6-membered heteroaryl groups for $R^2$ and $R^3$ are unsusbtituted or substituted by halogen, cyano, lower alkyl optionally substituted by one or more halogen atoms, lower alkoxy, $S(O)_2$-alkyl, S(O)-alkyl, or $-C(O)R'$ wherein R' is lower alkyl, lower alkoxy or $NR_2$; and n is 0, 1 or 2;

or a pharmaceutically acceptable salt thereof.

2. A compound of claim 1
wherein
$R^1$ is hydrogen or lower alkyl;
$R^2$ is aryl or is 5- or 6-membered heteroaryl selected from the group consisting of imidazolyl, isoxazolyl, pyrazolvl, pyridinyl, thiadiazolyl, and thiazolyl;
$R^3$ is hydrogen, aryl or 5- or 6-membered heteroaryl;
wherein the aryl or 5- or 6-membered heteroaryl groups for $R^2$ and $R^3$ are unsusbtituted or substituted by halogen, lower alkyl optionally substituted by one or more halogen atoms, lower alkoxy, $-C(O)O$-lower alkyl or cyano.

3. A compound of claim 1 wherein $R^3$ is hydrogen.

4. A compound of claim 3, wherein $R^3$ is hydrogen and $R^2$ is 5- or 6-membered substituted heteroaryl selected from the group consisting of imidazolyl, isoxazolyl, pyrazolvl, pyridinyl, thiadiazolyl, and thiazolyl.

5. A compound of claim 4, selected from the group consisting of
(6-methyl-pyridin-2-yl)-[1,7]naphthyridin-8-yl-amine,
(4-methyl-thiazol-2-yl)-[1,7]naphthyridin-8-yl-amine,
(2-Methyl-[1,7]naphthyridin-8-yl)-(4-methyl-thiazol-2-yl)-amine,
(5-Chloro-pyridin-2-yl)-(2-methyl-[1,7]naphthyridin-8-yl)-amine,
(5-Fluoro-pyridin-2-yl)-(2-methyl-[1,7]naphthyridin-8-yl)-amine,
(2-Chloro-pyridin-4-yl)-(2-methyl-[1,7]naphthyridin-8-yl)-amine,
(2-Methyl-[1,7]naphthyridin-8-yl)-(1-methyl-1H-pyrazol-3-yl)-amine,
(2-Methyl-[1,7]naphthyridin-8-yl)-(2-methyl-thiazol-4-yl)-amine,
(2-Chloro-[1,7]naphthyridin-8-yl)-(4-methyl-thiazol-2-yl)-amine,
(2-Chloro-[1,7]naphthyridin-8-yl)-(2-methyl-thiazol-4-yl)-amine,
(2-Methoxy-[1,7]naphthyridin-8-yl)-(4-methyl-thiazol-2-yl)-amine, and
(2-Ethyl-[1,7]naphthyridin-8-yl)-(4-methyl-thiazol-2-yl)-amine.

6. A compound of claim 3, wherein $R^3$ is hydrogen and $R_2$ is substituted aryl.

7. A compound of claim 6, selected from the group consisting of (3-chloro-phenyl)-[1,7]naphthyridin-8-yl-amine, and (3-Chloro-phenyl)-(2-methyl-[1,7]naphthyridin-8-yl)-amine.

8. A compound of claim 1, wherein $R^3$ is an optionally substituted 5- or 6-membered heteroaryl group.

9. A compound of claim 8, wherein $R^3$ and $R^2$ are both 5- or 6-membered substituted heteroaryl.

10. A compound of claim 9, selected from the group consisting of
- (6-methyl-pyridin-2-yl)-(5-pyridin-3-yl-[1,7]naphthyridin-8-yl)-amine,
- (2-chloro-pyridin-4-yl)-(5-pyridin-3-yl-[1,7]naphthyridin-8-yl)-amine,
- (5-methyl-pyridin-2-yl)-(5-pyridin-3-yl-[1,7]naphthyridin-8-yl)-amine,
- (5-fluoro-pyridin-2-yl)-(5-pyridin-3-yl-[1,7]naphthyridin-8-yl)-amine,
- (2-chloro-pyridin-4-yl)-[5-(6-methoxy-pyridin-3-yl)-[1,7]naphthyridin-8-yl]-amine,
- (2-chloro-pyridin-4-yl)-[5-(5-fluoro-pyridin-3-yl)-[1,7]naphthyridin-8-yl]-amine,
- (5-fluoro-pyridin-2-yl)-[5-(5-fluoro-pyridin-3-yl)-[1,7]naphthyridin-8-yl]-amine,
- (5-fluoro-pyridin-2-yl)-[5-(5-methoxy-pyridin-3-yl)-[1,7]naphthyridin-8-yl]-amine,
- (2-chloro-pyridin-4-yl)-(5-pyrimidin-5-yl-[1,7]naphthyridin-8-yl)-amine,
- (5-fluoro-pyridin-2-yl)-(5-pyrimidin-5-yl-[1,7]naphthyridin-8-yl)-amine, and
- (4-Methyl-thiazol-2-yl)-(5-pyrimidin-5-yl-[1,7]naphthyridin-8-yl)-amine.

11. A compound of claim 9, selected from the group consisting of
- (4-Methyl-thiazol-2-yl)-(5-pyridin-3-yl-[1,7]naphthyridin-8-yl)-amine,
- (1-Methyl-1H-pyrazol-3-yl)-(5-pyridin-3-yl-[1,7]naphthyridin-8-yl)-amine,
- (2-Methyl-thiazol-4-yl)-(5-pyridin-3-yl-[1,7]naphthyridin-8-yl)-amine,
- (2-Methyl-thiazol-4-yl)-(5-pyrimidin-5-yl-[1,7]naphthyridin-8-yl)-amine,
- (2-Methyl-5-pyridin-3-yl-[1,7]naphthyridin-8-yl)-(4-methyl-thiazol-2-yl)-amine,
- (5-Fluoro-pyridin-2-yl)-(2-methyl-5-pyridin-3-yl-[1,7]naphthyridin-8-yl)-amine,
- (2-Methyl-5-pyridin-3-yl-[1,7]naphthyridin-8-yl)-(2-methyl-thiazol-4-yl)-amine,
- (2-Chloro-pyridin-4-yl)-(2-methyl-5-pyridin-3-yl-[1,7]naphthyridin-8-yl)-amine,
- (2-Methyl-5-pyrimidin-5-yl-[1,7]naphthyridin-8-yl)-(2-methyl-thiazol-4-yl)-amine,
- [5-(6-Chloro-pyridin-3-yl)-2-methyl-[1,7]naphthyridin-8-yl]-(2-methyl-thiazol-4-yl)-amine, and
- [5-(6-Chloro-pyridin-3-yl)-2-methyl-[1,7]naphthyridin-8-yl]-(4-methyl-thiazol-2-yl)-amine.

12. A compound of claim 9, selected from the group consisting of [5-(3,5-Dimethyl-isoxazol-4-yl)-2-methyl-[1,7]naphthyridin-8-yl]-(4-methyl-thiazol-2-yl)-amine,
- [5-(2,5-Dimethyl-2H-pyrazol-3-yl)-2-methyl-[1,7]naphthyridin-8-yl]-(4-methyl-thiazol-2-yl)-amine,
- 5-[2-Methyl-8-(4-methyl-thiazol-2-ylamino)-[1,7]naphthyridin-5-yl]-pyridine-2-carbonitrile,
- (2-Methyl-5-pyrimidin-5-yl-[1,7]naphthyridin-8-yl)-(4-methyl-thiazol-2-yl)-amine,
- (2-Methyl-5-pyridin-4-yl-[1,7]naphthyridin-8-yl)-(4-methyl-thiazol-2-yl)-amine,
- [2-Methyl-5-(4-methyl-pyridin-3-yl)-[1,7]naphthyridin-8-yl]-(4-methyl-thiazol-2-yl)-amine,
- [5-(6-Fluoro-pyridin-3-yl)-2-methyl-[1,7]naphthyridin-8-yl]-(4-methyl-thiazol-2-yl)-amine,
- [5-(6-Methoxy-pyridin-3-yl)-2-methyl-[1,7]naphthyridin-8-yl]-(4-methyl-thiazol-2-yl)-amine,
- [5-(5-Methoxy-pyridin-3-yl)-2-methyl-[1,7]naphthyridin-8-yl]-(4-methyl-thiazol-2-yl)-amine,
- [2-Methyl-5-(3-methyl-pyridin-2-yl)-[1,7]naphthyridin-8-yl]-(4-methyl-thiazol-2-yl)-amine, and
- (2-Methyl-5-pyrimidin-5-yl-[1,7]naphthyridin-8-yl)-(4-trifluoromethyl-thiazol-2-yl)-amine.

13. A compound of claim 9, selected from the group consisting of
- (4-Chloro-thiazol-2-yl)-(2-methyl-5-pyrimidin-5-yl-[1,7]naphthyridin-8-yl)-amine,
- [5-(5-Fluoro-pyridin-3-yl)-2-methyl-[1,7]naphthyridin-8-yl]-(4-methyl-thiazol-2-yl)-amine,
- [2-Methyl-5-(6-methyl-pyridin-3-yl)-[1,7]naphthyridin-8-yl]-(4-methyl-thiazol-2-yl)-amine,
- (2-Methyl-pyrimidin-4-yl)-(2-methyl-5-pyrimidin-5-yl-[1,7]naphthyridin-8-yl)-amine,
- (2-Chloro-pyridin-4-yl)-(2-methyl-5-pyrimidin-5-yl-[1,7]naphthyridin-8-yl)-amine,
- [5-(2,5-Dimethyl-2H-pyrazol-3-yl)-2-methyl-[1,7]naphthyridin-8-yl]-(2-methyl-thiazol-4-yl)-amine,
- (2-Methyl-5-pyrimidin-2-yl-[1,7]naphthyridin-8-yl)-(2-methyl-thiazol-4-yl)-amine,
- [2-Methyl-5-(2-methyl-pyridin-3-yl)-[1,7]naphthyridin-8-yl]-(2-methyl-thiazol-4-yl)-amine,
- (1-Methyl-1H-pyrazol-3-yl)-(2-methyl-5-pyrimidin-5-yl-[1,7]naphthyridin-8-yl)-amine,
- [5-(5-Fluoro-pyridin-3-yl)-2-methyl-[1,7]naphthyridin-8-yl]-(1-methyl-1H-pyrazol-3-yl)-amine, and
- [2-Methyl-5-(6-methyl-pyridin-2-yl)-[1,7]naphthyridin-8-yl]-(2-methyl-thiazol-4-yl)-amine.

14. A compound of claim 9, selected from the group consisting of (4-Methyl-thiazol-2-yl)-(2-methyl-5-thiazol-2-yl-[1,7]naphthyridin-8-yl)-amine,
- [2-Methyl-5-(3-methyl-3H-imidazol-4-yl)-[1,7]naphthyridin-8-yl]-(4-methyl-thiazol-2-yl)-amine,
- [2-Methyl-5-(3-methyl-3H-imidazol-4-yl)-[1,7]naphthyridin-8-yl]-(2-methyl-thiazol-4-yl)-amine,
- [2-Methyl-5-(3-methyl-[1,2,4]thiadiazol-5-yl)-[1,7]naphthyridin-8-yl]-(2-methyl-thiazol-4-yl)-amine,
- [2-Methyl-5-(2-methyl-pyrimidin-5-yl)-[1,7]naphthyridin-8-yl]-(2-methyl-thiazol-4-yl)-amine,
- (2-Methyl-5-pyrazin-2-yl-[1,7]naphthyridin-8-yl)-(2-methyl-thiazol-4-yl)-amine,
- [5-(5-Fluoro-pyridin-3-yl)-2-methyl-[1,7]naphthyridin-8-yl]-(2-methyl-thiazol-4-yl)-amine,
- (2-Methyl-5-pyridin-3-yl-[1,7]naphthyridin-8-yl)-(4-trifluoromethyl-thiazol-2-yl)-amine,
- (4-Difluoromethyl-thiazol-2-yl)-(2-methyl-5-pyridin-3-yl-[1,7]naphthyridin-8-yl)-amine, (4-Methyl-thiazol-2-yl)-[2-methyl-5-(5-trifluoromethyl-pyridin-3-yl)-[1,7]naphthyridin-8-yl]-amine, and
- (4-Methyl-thiazol-2-yl)-[2-methyl-5-(6-trifluoromethyl-pyrazin-2-yl)-[1,7]naphthyridin-8-yl]-amine.

15. A compound of claim 8, wherein $R^3$ is 5- or 6-membered substituted heteroaryl and $R^2$ is substituted aryl.

16. A compound of claim 15, selected from the group consisting of
- (3-chloro-phenyl)-(5-pyridin-3-yl-[1,7]naphthyridin-8-yl)-amine and
- (3-chloro-phenyl)-[5-(6-chloro-pyridin-3-yl)-[1,7]naphthyridin-8-yl]-amine.

17. A compound of claim 1, wherein $R^3$ is optionally substituted aryl.

18. A compound of claim 17, wherein $R^3$ is substituted aryl and $R^2$ is 5- or 6-membered substituted heteroaryl.

19. A compound of claim 18, selected from the group consisting of:
- [5-(3-Methoxy-phenyl)-2-methyl-[1,7]naphthyridin-8-yl]-(4-methyl-thiazol-2-yl)-amine, (4-Methyl-thiazol-2-yl)-[2-methyl-5-(3-trifluoromethyl-phenyl)-[1,7]naphthyridin-8-yl]-amine,

[5-(3-Methanesulfonyl-phenyl)-2-methyl-[1,7]naphthyridin-8-yl]-(4-methyl-thiazol-2-yl)-amine, and

[5-(3-Fluoro-phenyl)-2-methyl-[1,7]naphthyridin-8-yl]-(1-methyl-1H-pyrazol-3-yl)-amine.

20. A pharmaceutical composition comprising a therapeutically effective amount of a compound of formula I

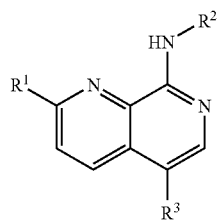

wherein $R^1$ is hydrogen, halogen, cyano, lower alkoxy, lower alkyl, lower alkyl substituted by halogen, cycloalkyl, —(CH$_2$)—O-lower alkyl, or —C(O)R' wherein R' is lower alkyl, lower alkoxy or NR$_2$;

R is hydrogen or lower alkyl;

$R^2$ is aryl or is 5- or 6-membered heteroaryl selected from the group consisting of imidazolyl, isoxazolyl, pyrazolyl, pyridinyl, thiadiazolyl, and thiazolyl;

$R^3$ is hydrogen, OR, NR$_2$, lower alkyl, cycloalkyl, aryl, heterocycloalkyl, 5- or 6-membered heteroaryl, C(O)NR$_2$, lower alkyl substituted by halogen, or —C(O)R' wherein R' is lower alkyl, lower alkoxy or NR$_2$;

wherein the aryl, cycloalkyl, heterocycloalkyl or 5- or 6-membered heteroaryl groups for $R^2$ and $R^3$ are unsusbtituted or substituted by halogen, cyano, lower alkyl optionally substituted by one or more halogen atoms, lower alkoxy, S(O)$_2$-alkyl, S(O)-alkyl, or —C(O)R' wherein R' is lower alkyl, lower alkoxy or NR$_2$; and n is 0, 1 or 2;

or a pharmaceutically acceptable salt thereof and a pharmaceutically acceptable carrier.

* * * * *